US012721854B2

(12) United States Patent
Dumoulin-White et al.

(10) Patent No.: US 12,721,854 B2
(45) **Date of Patent: *Sep. 1, 2026**

(54) INACTIVATION OF PATHOGENS USING METAL-BASED COORDINATION COMPLEXES, AND METHODS AND COMPOSITIONS FOR TREATING AND PREVENTING MICROBIAL AND/OR VIRAL INFECTIONS

(71) Applicant: Theralase Technologies, Inc., Toronto (CA)

(72) Inventors: Roger Dumoulin-White, Toronto (CA); Arkady Mandel, North York (CA)

(73) Assignee: Theralase Technologies, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/192,597

(22) Filed: Mar. 4, 2021

(65) Prior Publication Data

US 2022/0280529 A1 Sep. 8, 2022

(51) Int. Cl.

*A61K 31/555* (2006.01)
*A61K 39/00* (2006.01)
*A61K 39/125* (2006.01)

(52) U.S. Cl.

CPC .......... *A61K 31/555* (2013.01); *A61K 39/125* (2013.01); *A61K 39/00* (2013.01); *A61K 2039/5254* (2013.01)

(58) Field of Classification Search

CPC ................ A61K 31/555; A61K 39/125; A61K 2039/5254; A61K 39/00; Y02A 50/30

See application file for complete search history.

(56) References Cited

U.S. PATENT DOCUMENTS

| | | | | |
|---|---|---|---|---|
| 6,962,910 | B2 | 11/2005 | Brewer et al. | |
| 7,612,057 | B2 | 11/2009 | Brewer et al. | |
| 8,148,360 | B2 | 4/2012 | Brewer et al. | |
| 8,445,475 | B2 | 5/2013 | Brewer et al. | |
| 8,834,899 | B2 | 9/2014 | Friedberg | |
| 10,111,936 | B2 | 10/2018 | Mandel | |
| 10,335,608 | B2 | 7/2019 | Mandel et al. | |
| 11,020,475 | B1 * | 6/2021 | Seo | A61P 31/14 |
| 11,464,798 | B2 * | 10/2022 | Mandel | A61K 39/4622 |
| 2007/0212379 | A1 * | 9/2007 | Goodrich | C12N 7/00 424/277.1 |
| 2012/0088729 | A1 | 4/2012 | Zhang et al. | |
| 2016/0206653 | A1 | 7/2016 | Mandel | |
| 2021/0369835 | A1 * | 12/2021 | Forrest | A61K 39/215 |

FOREIGN PATENT DOCUMENTS

| | | | | |
|---|---|---|---|---|
| WO | 2013158550 A1 | | 10/2013 | |
| WO | 2014145428 A2 | | 9/2014 | |
| WO | WO-2018209203 A1 | * | 11/2018 | A61K 31/4745 |

OTHER PUBLICATIONS

Pacific Immunology, Antigens vs Immunogens. Retrieved from the Internet on Nov. 28, 2022, https://www.pacificimmunology.com/resources/antigens/antigens-vs-immunogens/#:~: text=An%20immunogen%20refers%20to%20a,not%20necessarily%20be%20an%20immunogen. (Year: 2022).*

Translation of CN 112107683. Published Dec. 22, 2020. Retrieved from Google Patents on Jan. 5, 2023, https://patents.google.com/patent/CN112107683A/en?q=(%22photodynamic%22+virus+vaccine)&oq=(%22photodynamic%22+virus+vaccine) (Year: 2020).*

De Paiva et al. What is holding back the development of antiviral metallodrugs? A literature overview and implications for SARS-COV-2 therapeutics and future viral outbreaks. Royal Society of Chemistry. 202, 49, 16004-16033. (Year: 2020).*

Andrei, Graciela. Vaccines and Antivirals: Grand Challenges and Great Opportunities. Frontiers in Virology. vol. 1 (Year: 2021).*

McKenzi et al. Transition metal complexes as photosensitisers in one- and two-photon photodynamic therapy. Coordination Chemistry Reviews 379 (2019) 2-29. (Year: 2019).*

Arenas et al. Photodynamic inactivation of *Staphylococcus aureus* and methicillin-resistant *Staphylococcus aureus* with Ru(II)-based type1/type II photosensitizers. Photodiagnosis and Photodynamic Therapy, 10, 615-625. Published 2013. (Year: 2013).*

Rizvi et al. (2013). PDT Dose Parameters Impact Tumoricidal Durability and Cell Death Pathways in a 3D Ovarian Cancer Model. Photochemistry and Photobiology, 89, 942-952.

Steere et al. (2012). Biochemical and structural characterization of recombinant human serum transferrin from rice (*Oryza sativa* L.). J Inorg Biochem; 116C, 37-44.

Zhang et al. (2010). Expression, purification, and characterization of recombinant human transferrin from rice (*Oryza sativa* L.). Protein Expr Purif; 74(1), 69-79.

* cited by examiner

*Primary Examiner* — Lauren Wells

(74) *Attorney, Agent, or Firm* — Caesar Rivise, PC

(57) ABSTRACT

A method for eliciting an immune response in a patient includes the sequential steps of: providing an immunogenic composition including an immunogen; adding a metal-based coordination complex to the immunogenic composition to inactivate or attenuate the immunogen; and administering the immunogenic composition to the patient so as to elicit the immune response against the immunogen. A method for preparing an attenuated immunogenic composition includes the steps of: providing an immunogenic composition including an immunogen; and adding a metal-based coordination complex to the immunogenic composition to inactivate or attenuate the immunogen in the immunogenic composition to provide the attenuated immunogenic composition.

24 Claims, 5 Drawing Sheets

Fig. 2
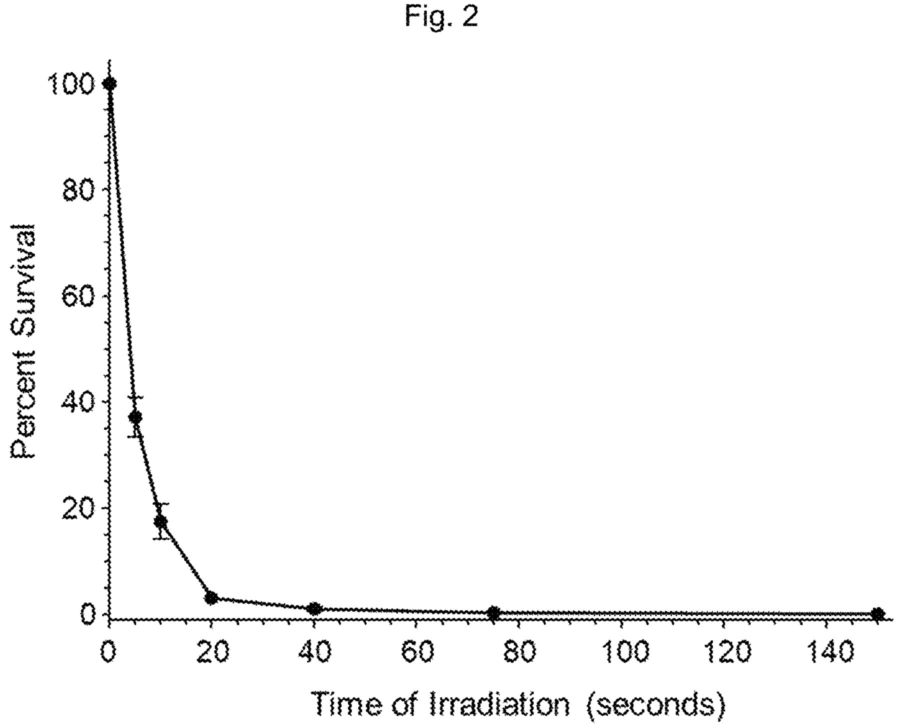
Fig. 3A
Fig. 3B
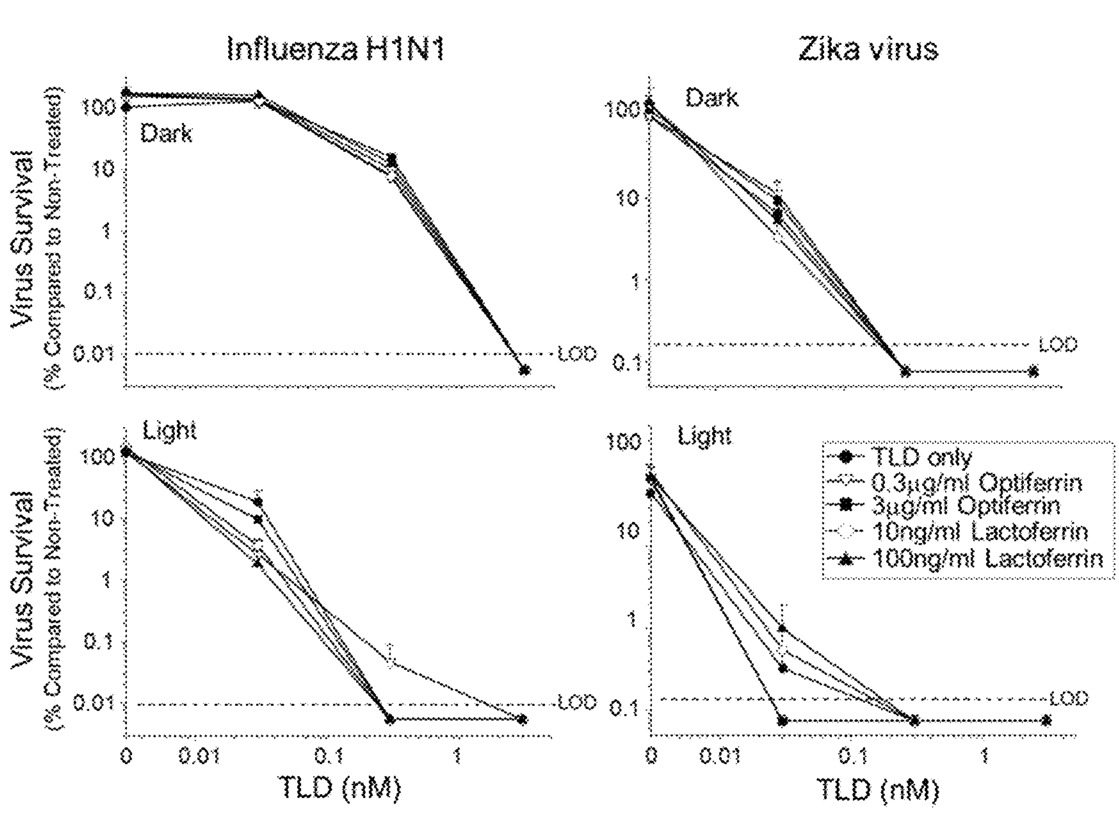
Fig. 3C
Fig. 3D

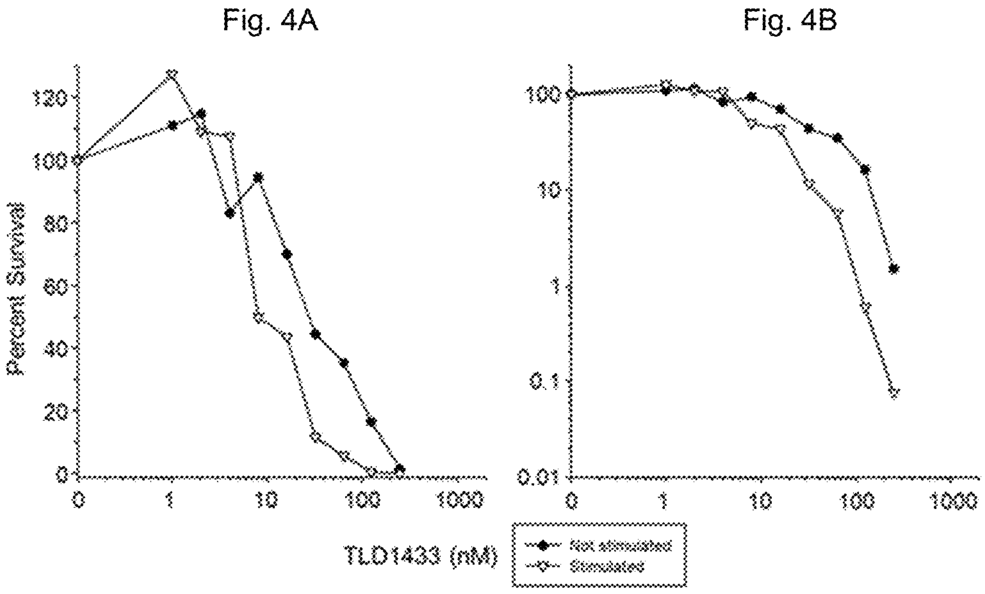
Fig. 4A
Fig. 4B
Percent Survival
TLD1433 (nM)
Not stimulated
Stimulated
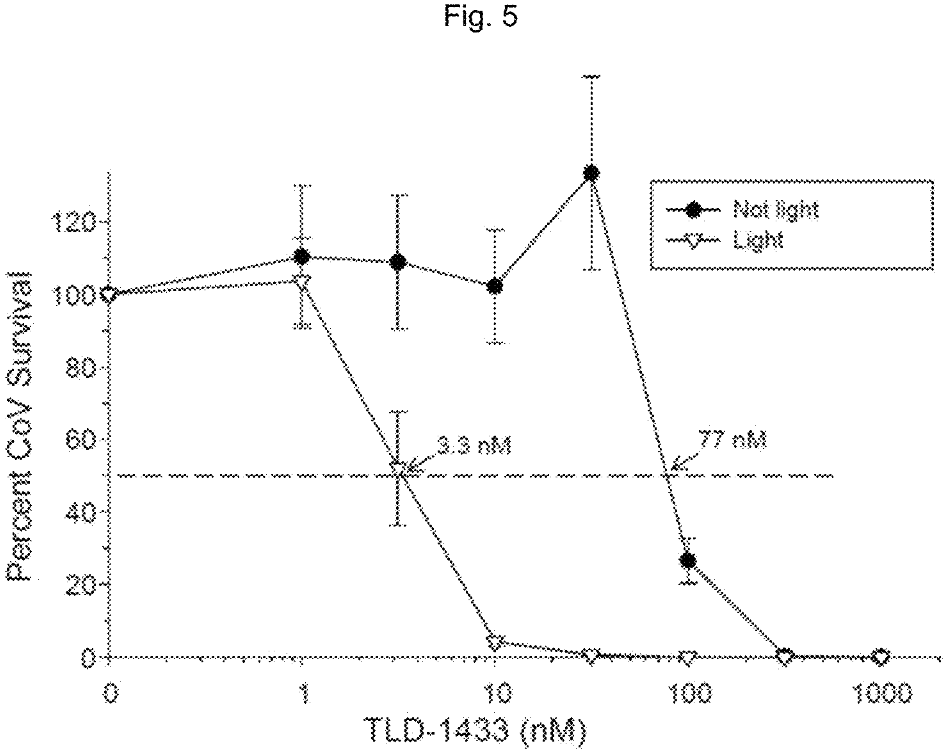
Fig. 5
Percent CoV Survival
TLD-1433 (nM)
Not light
Light
3.3 nM
77 nM Fig. 6
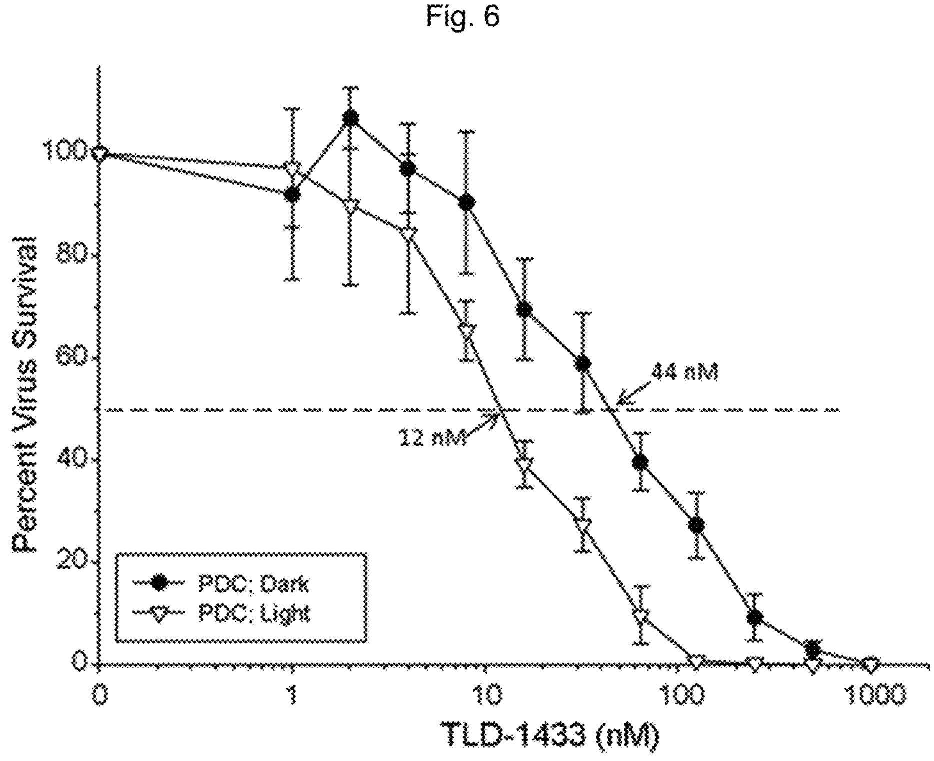
Fig. 7A
Fig. 7B
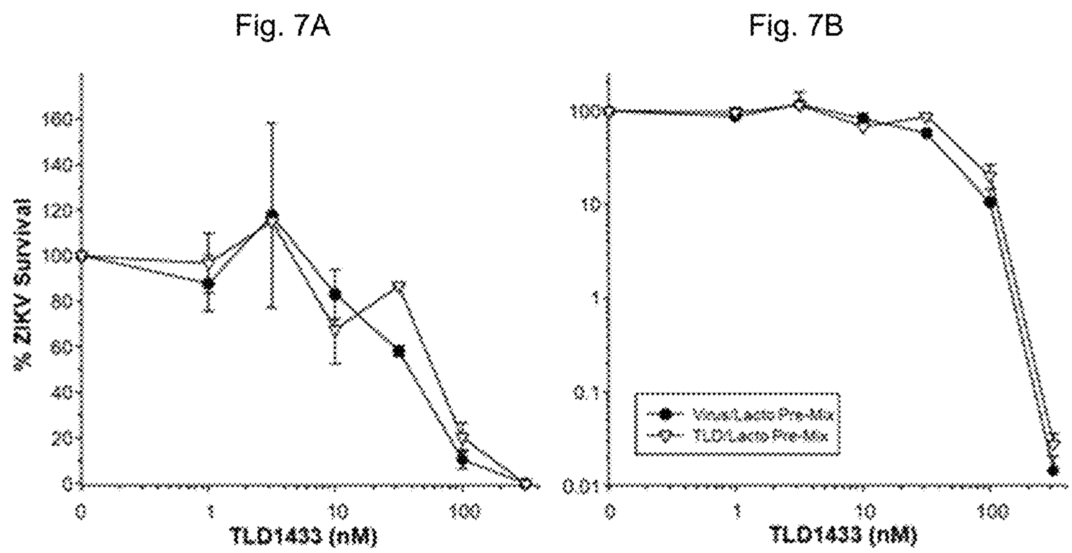

INACTIVATION OF PATHOGENS USING METAL-BASED COORDINATION COMPLEXES, AND METHODS AND COMPOSITIONS FOR TREATING AND PREVENTING MICROBIAL AND/OR VIRAL INFECTIONS

BACKGROUND OF THE INVENTION

1. Field of Invention

This invention relates to methods and compositions for treating and preventing infections caused by a pathogen, such as a virus or microbe, particularly coronavirus infections, including the SARS-CoV-2 virus.

2. Description of Related Art

COVID-19, the disease caused by the SARS-CoV-2 virus, first presented in Wuhan, Hubei province, China in December 2019. Since then, it has rapidly spread across the world and is now formally considered a pandemic.

The enormous worldwide health, economic and social impact make it paramount to address the prophylactics and active treatment of COVID-19 and its associated variants.

It has been demonstrated that the infection rates, severity and lethality are substantially higher in the immunocompromised individuals and population aged 60 and older. This could be partially due to comorbidity and partially due to immunosenescence, a progressive decline in both innate and acquired immune function in the chronically ill patients and elderly, as well as due to a general loss of function or fitness. Immunosenescence is a major factor affecting vaccination response, as well as the severity and lethality of infectious diseases.

While vaccination reduces infection rates and therapeutic interventions reduce the severity and lethality of infections, these interventions have limitations in immunocompromised patients. This impaired ability to mount an efficient immune response after exposure to infectious agents or vaccines represents a major challenge in acquiring protection against COVID-19.

Photo Dynamic Therapy ("PDT") is a form of phototherapy which combines a photosynthesizing chemical substance and light to product singlet oxygen and/or Reactive Oxygen Species ("ROS") to elicit cell death. The development of new Photo Dynamic Compounds ("PDCs") or photosensitizers for PDT has been increasingly focused on metallosupramolecular complexes derived from metals. For example, WO 2013158550 A1 and WO 2014145428 A2 disclose metal-based PDCs useful as in vivo diagnostic agents, therapeutic agents for treating or preventing diseases that involve unwanted and/or hyperproliferating cell etiology (including cancer), agents for treating infectious diseases and agents for pathogen disinfection and/or sterilization. U.S. Pat. Nos. 6,962,910, 7,612,057, 8,445,475 and 8,148,360 disclose supramolecular metal complexes capable of cleaving DNA when irradiated with visible light with or without the presence of molecular oxygen.

Delivery of metal-based coordination complexes and PDCs to biological targets can pose a challenge, which many have attempted to address. See, e.g., U.S. Pat. No. 10,111,936 B2, and the references cited therein.

Use of PDT in the preparation of vaccines is known. For example, U.S. Pat. No. 8,834,899 B2 discloses a vaccine for mesothelioma generated using PDT and its use in methods and compositions for treating mesothelioma.

Despite the foregoing developments, it is desired to provide vaccines, prophylactic and therapeutic methods that stimulate the compromised immune system, thus promoting more successful prophylaxis and treatment of viruses, and more particular coronaviruses, including SARS-CoV-2 and its associated variants.

BRIEF SUMMARY OF THE INVENTION

A first aspect of the invention is a method for eliciting an immune response in a patient, said method comprising the sequential steps of: providing an immunogenic composition comprising an immunogen; adding a metal-based coordination complex to the immunogenic composition to inactivate or attenuate the immunogen; and administering the immunogenic composition to the patient so as to elicit the immune response against the immunogen.

In certain embodiments of the first aspect of the invention, the metal-based coordination complex is represented by one of the following formulas:

(a) formula (I):

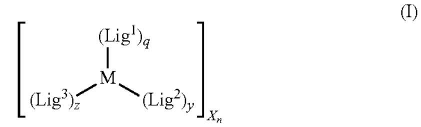

(I)

including hydrates, solvates, pharmaceutically acceptable salts, prodrugs and complexes thereof, wherein:

M at each occurrence is independently selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

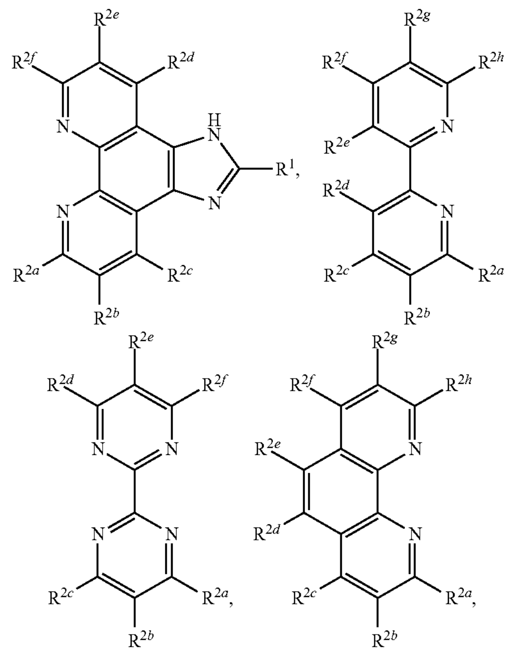

-continued
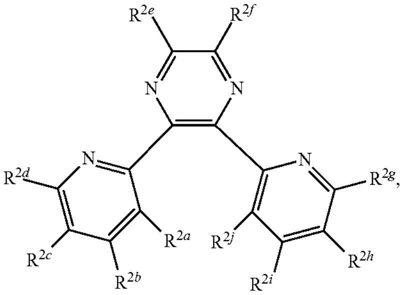
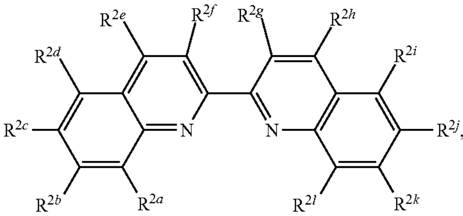
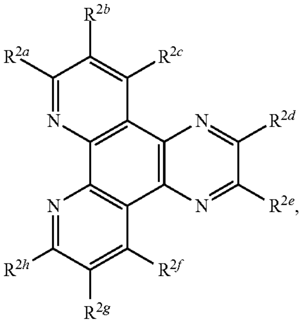
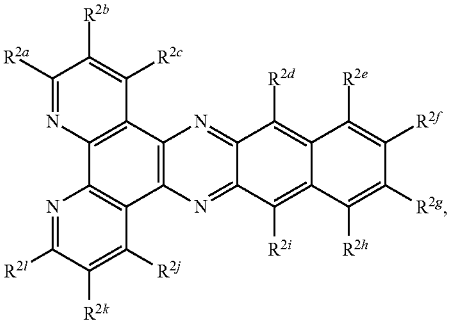
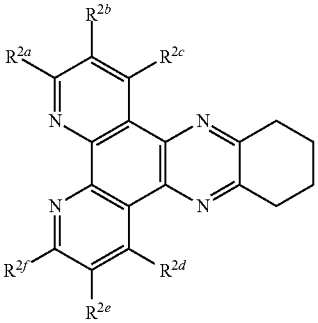
,
-continued
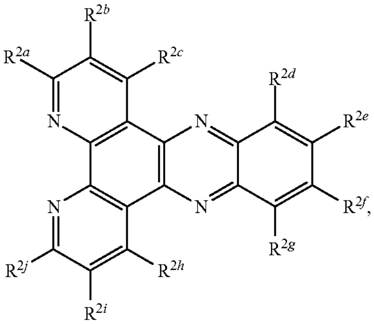
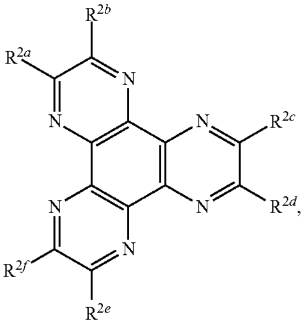
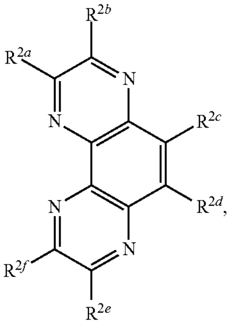
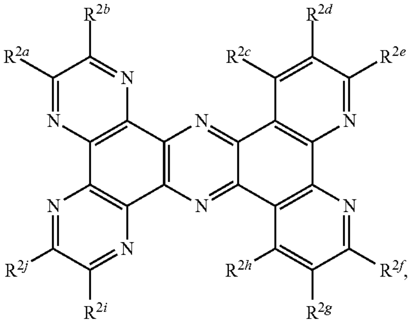
and
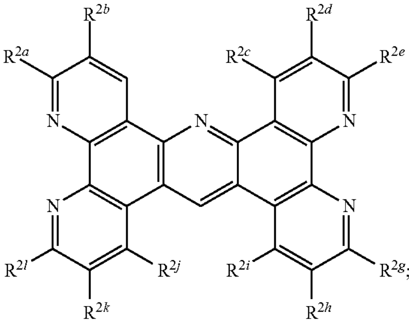
$Lig^2$ is a bidentate ligand that at each occurrence is each independently selected from the group consisting of -continued
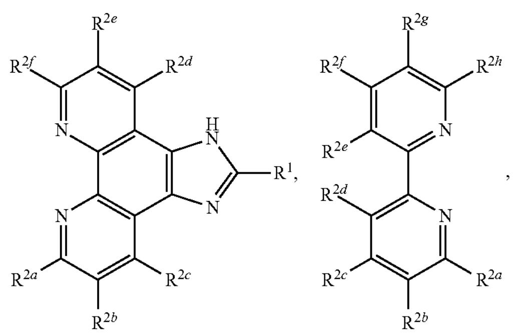
,
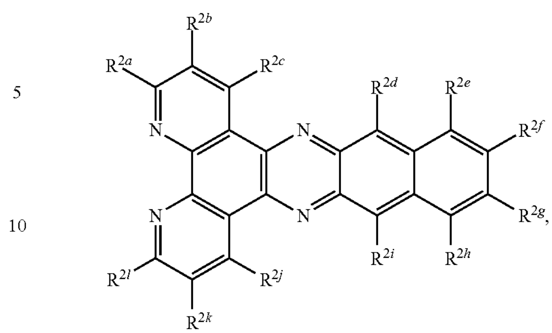
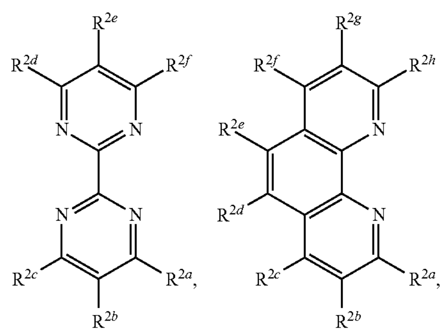
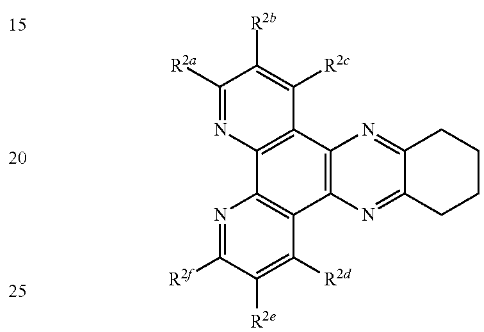
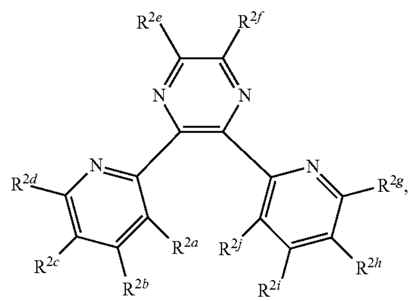
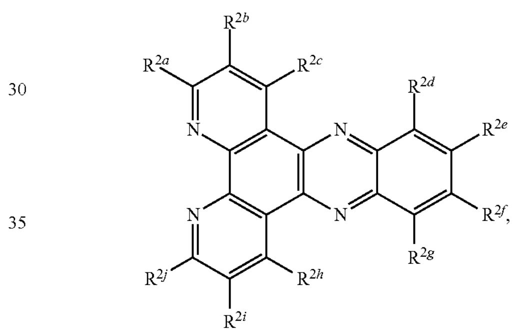
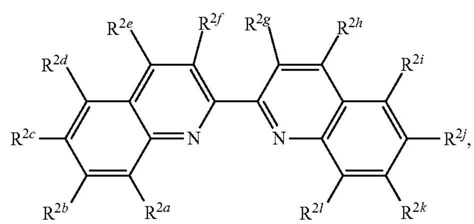
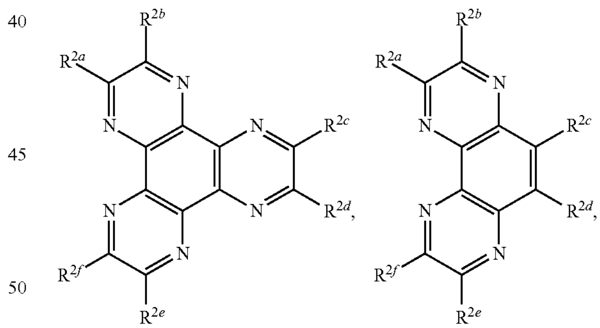
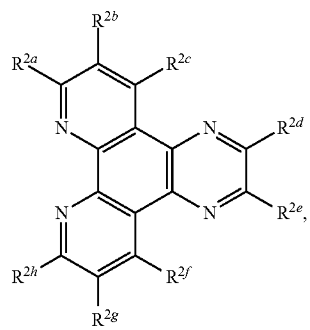
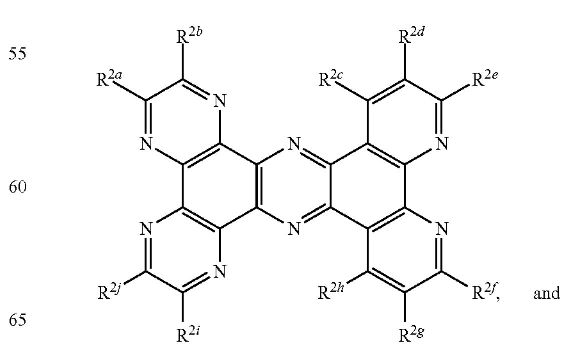
and -continued
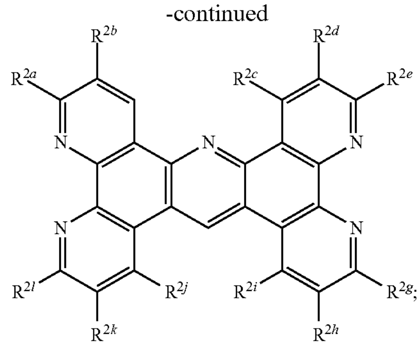
$Lig^3$ is a bidentate ligand that at each occurrence is each independently selected from the group consisting of
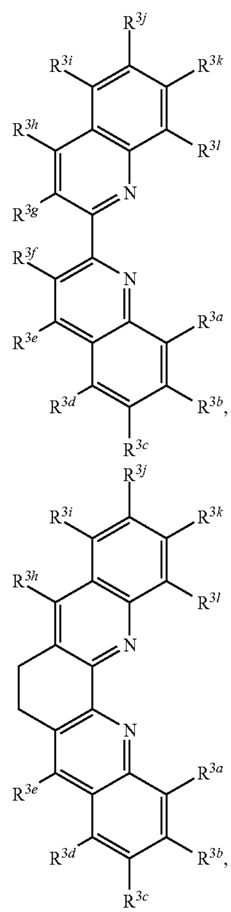
-continued
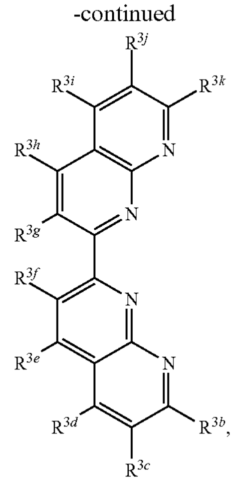
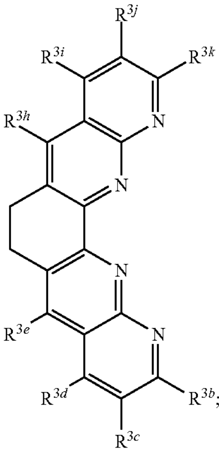
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
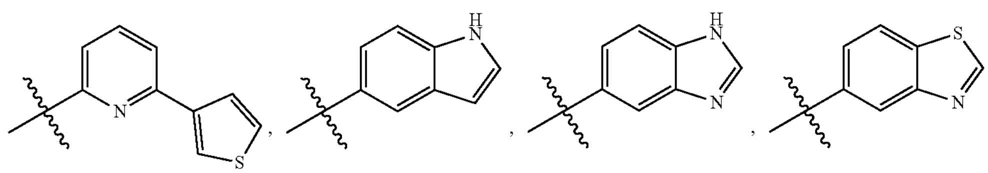

-continued

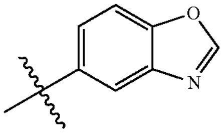,
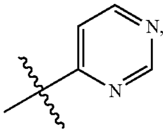,
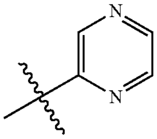,
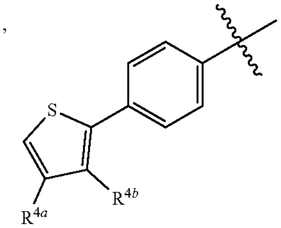,

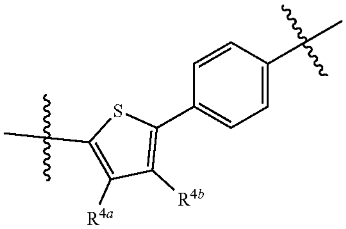,
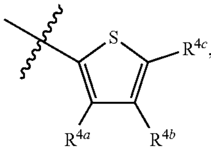,
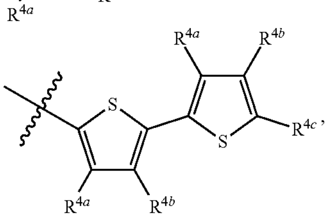,

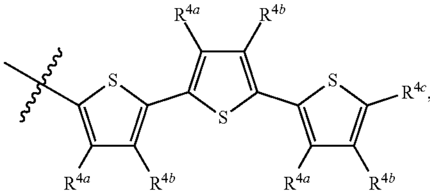,
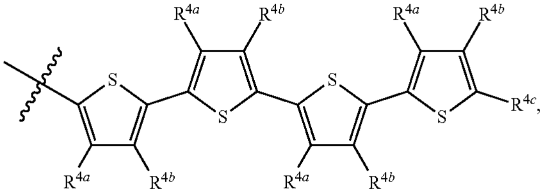,

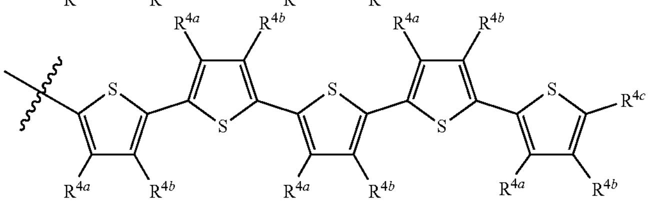

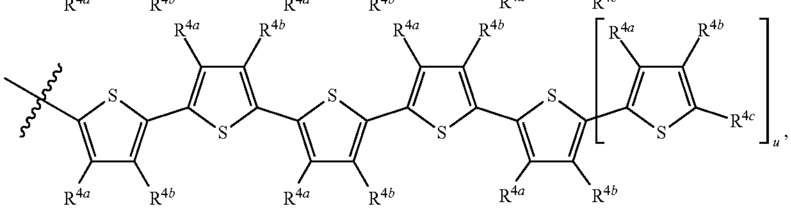,

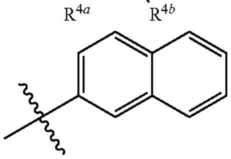,
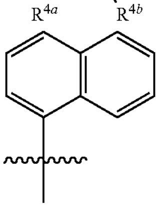,
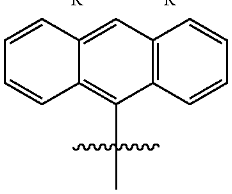,
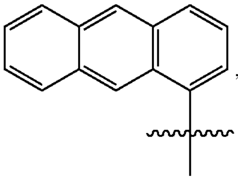,

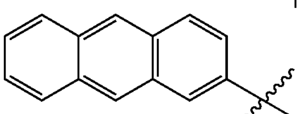, and
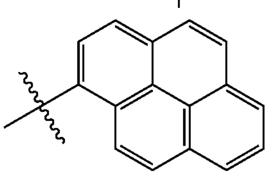;

u is an integer from 1 to 20;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

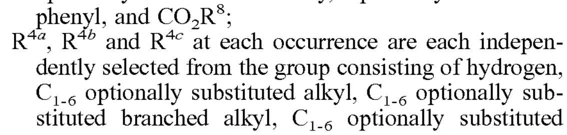

$R^{4a}$, $R^{4b}$ and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

-continued

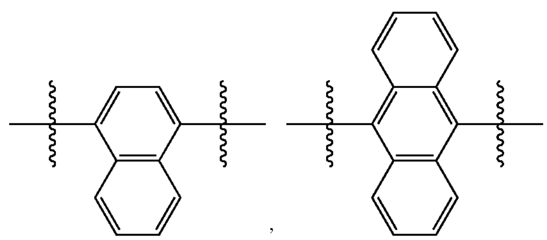

,

,

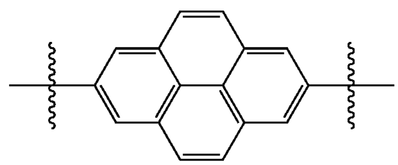

, (b) formula (VI):

(VI)

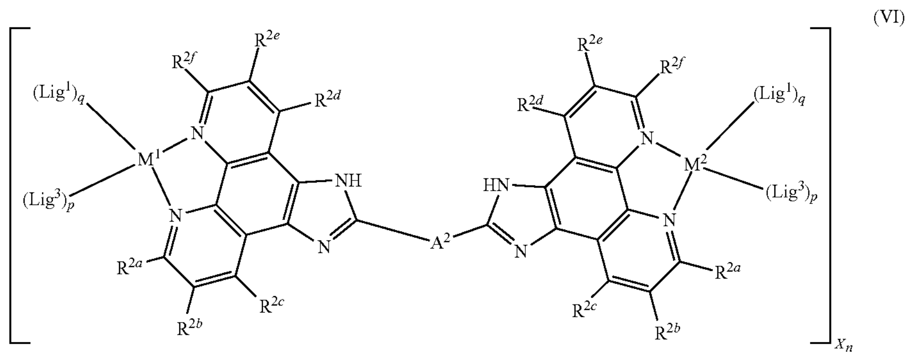

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

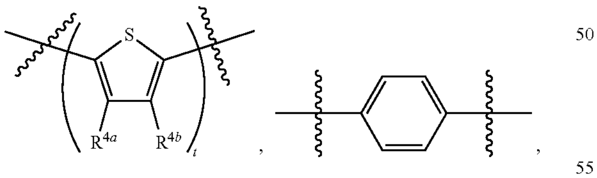

,

,

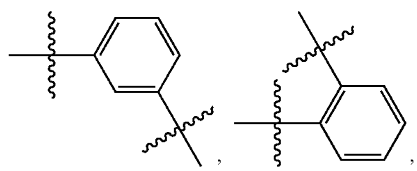

,

,

-continued

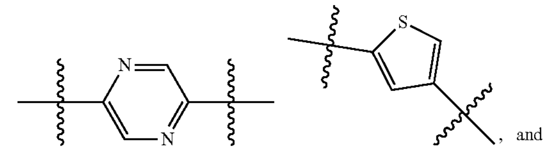

, and

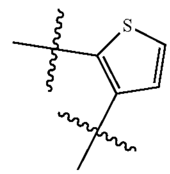

t is an integer;

(c) formula (VIIa):
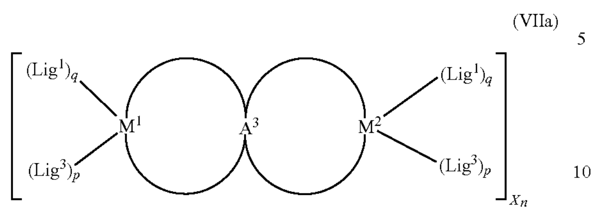
including hydrates, solvates, pharmaceutically acceptable salts, prodrugs and complexes thereof wherein:
$A^3$ is selected from the group consisting of
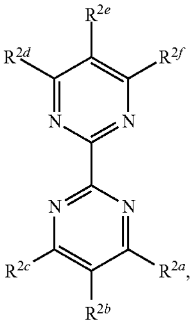
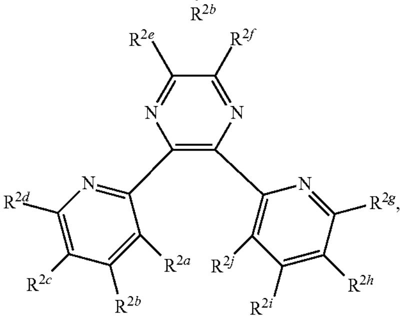
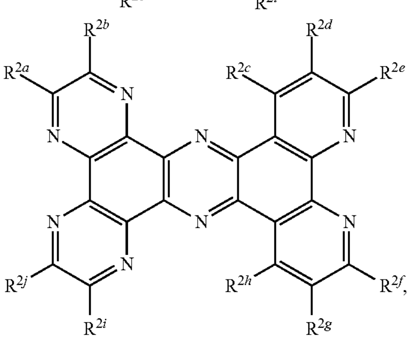
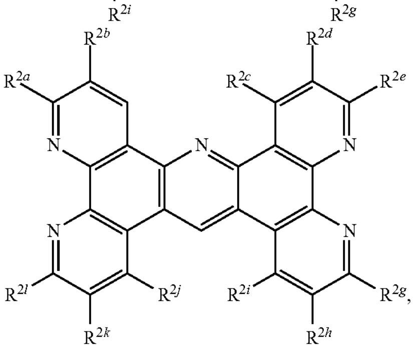
and
-continued
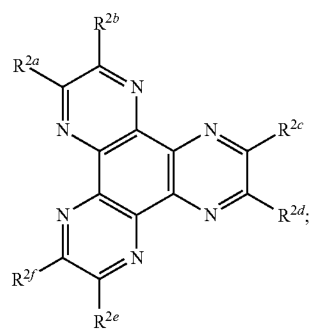
$Lig^1$ is a bidentate ligand that at each occurrence is each independently selected from the group consisting of
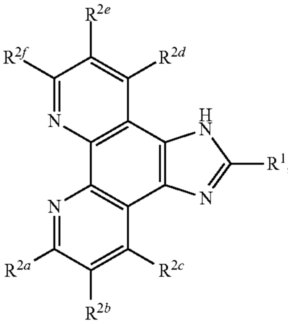
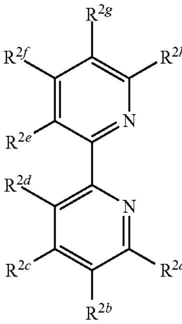
,
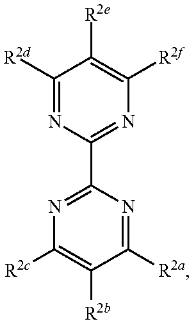
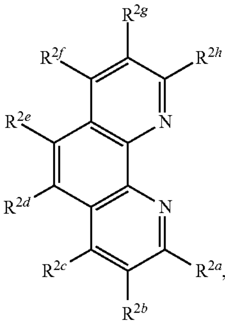
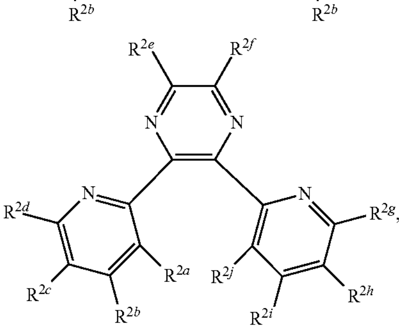
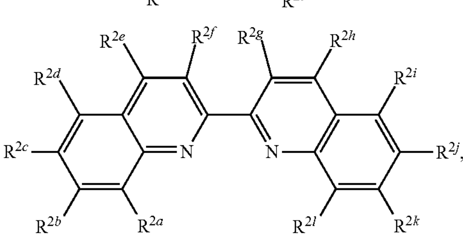

-continued
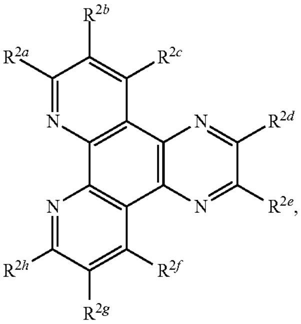
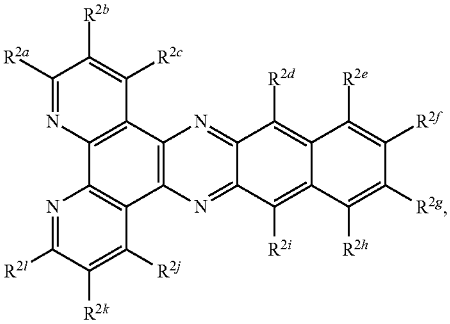
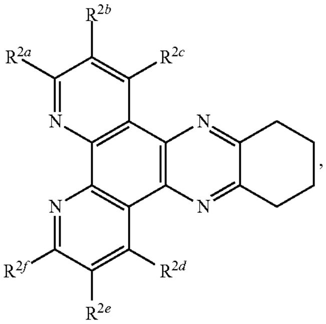
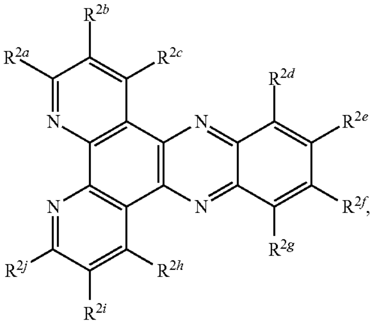
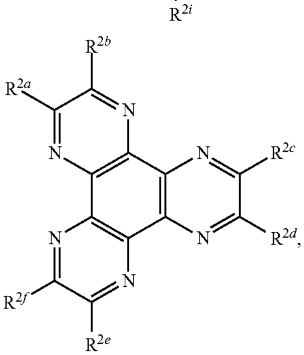
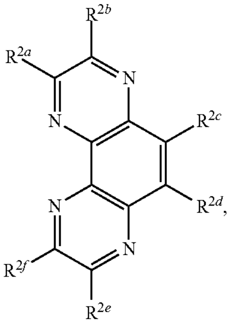
-continued
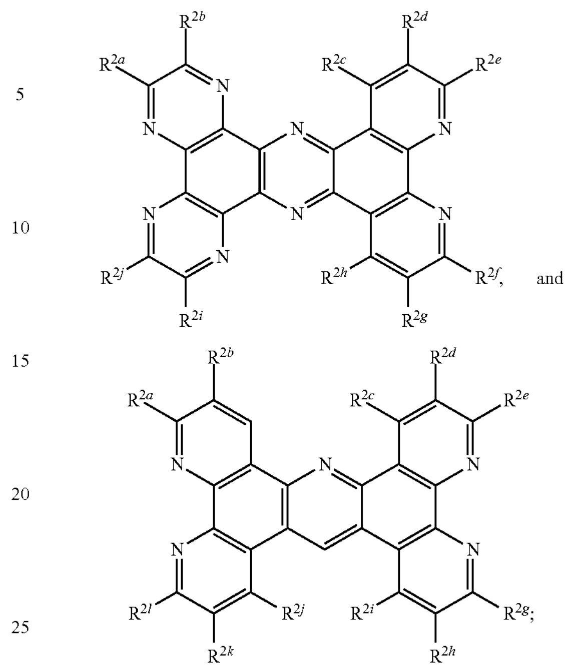
and
Lig$^3$ is a bidentate ligand that at each occurrence is each independently selected from the group consisting of
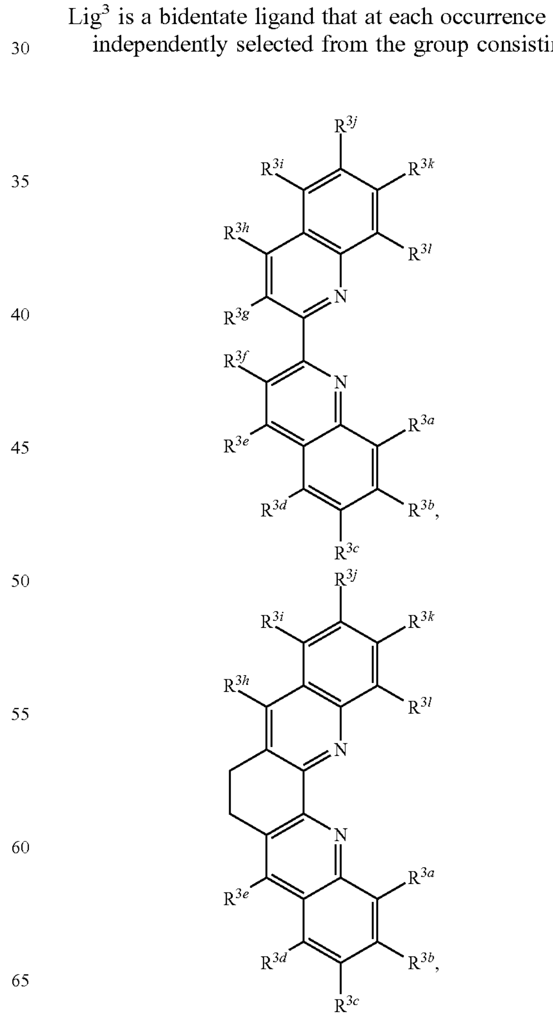

-continued
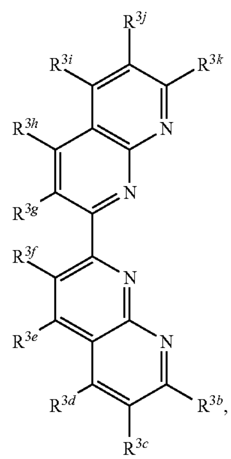
-continued
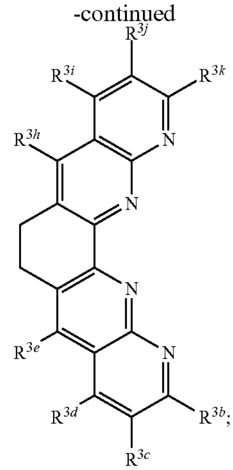
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
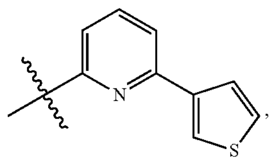,
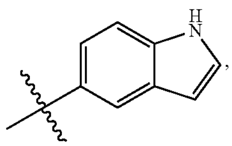,
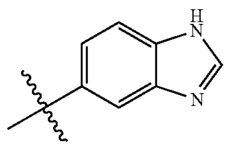,
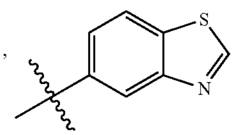,
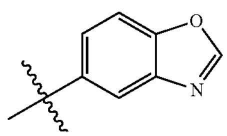,
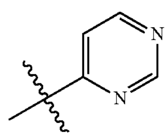,
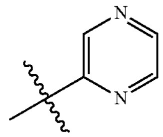,
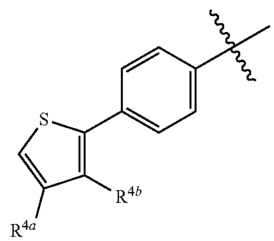,
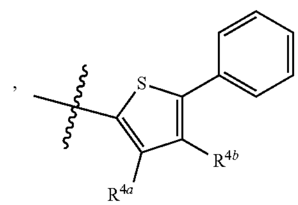,
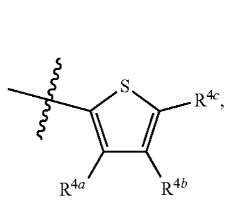,
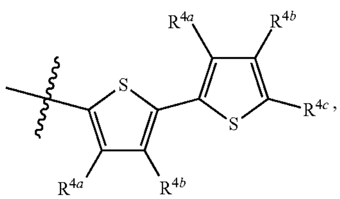,
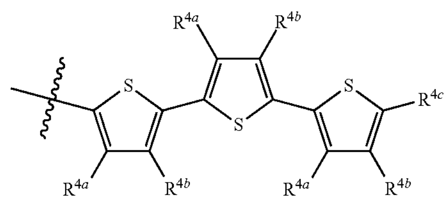, -continued

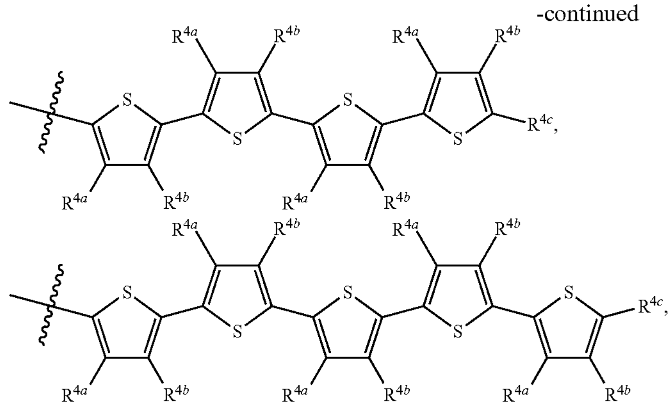

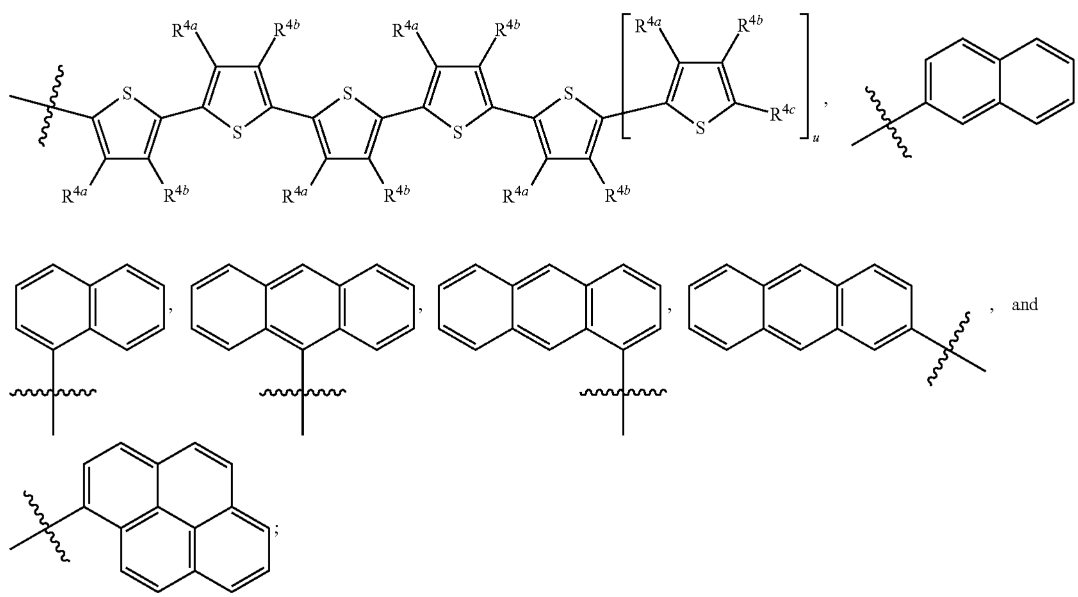

u is an integer from 1 to 20;

$R^{2a}$, $R^{2b}$, $R^{2c}$, $R^{2d}$, $R^{2e}$, $R^{2f}$, $R^{2g}$, $R^{h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl p is independently at each occurrence 0, 1, or 2;

q is independently at each occurrence 0, 1, or 2; and n is 0, 1, 2, 3, 4, or 5.

(d) formula (II):

(II)

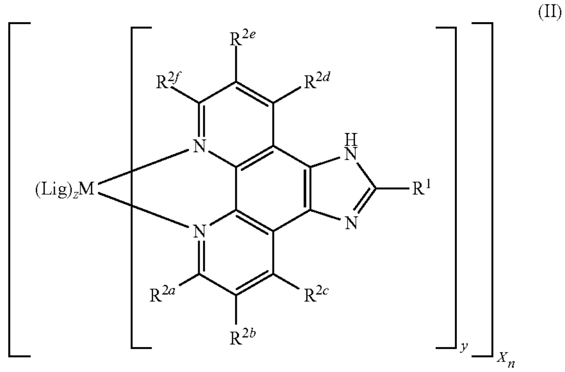

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

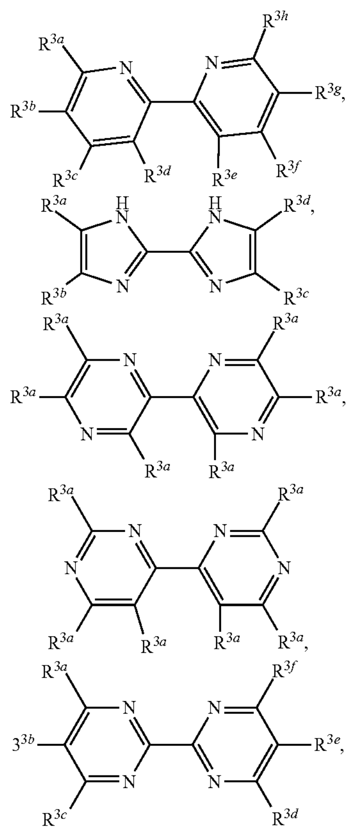

-continued

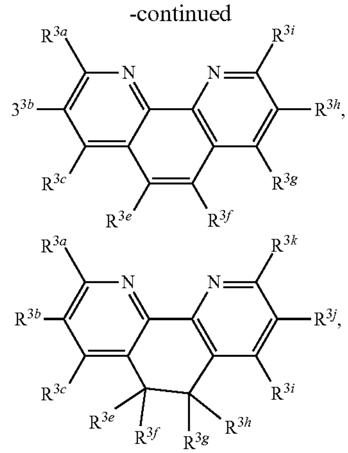

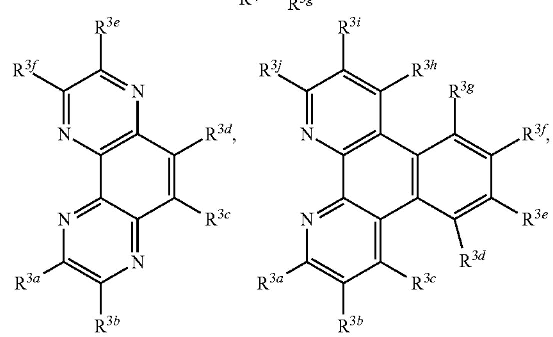

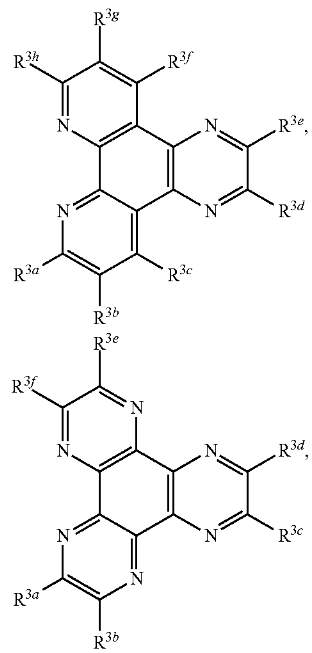

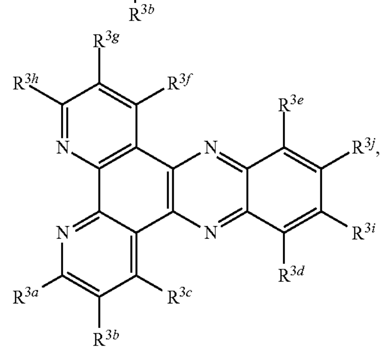

-continued

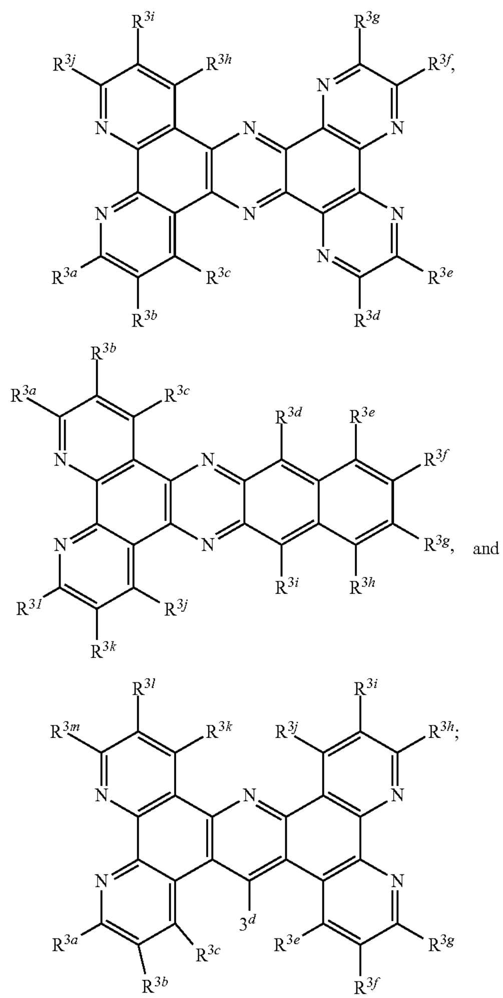

and

R¹ is selected from the group consisting of

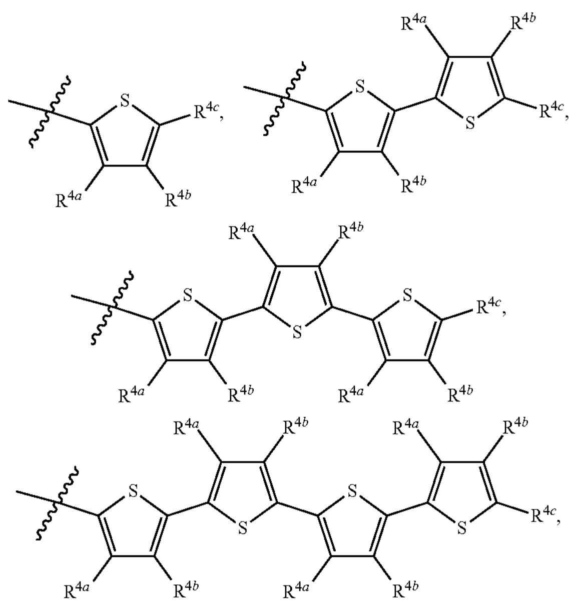

-continued

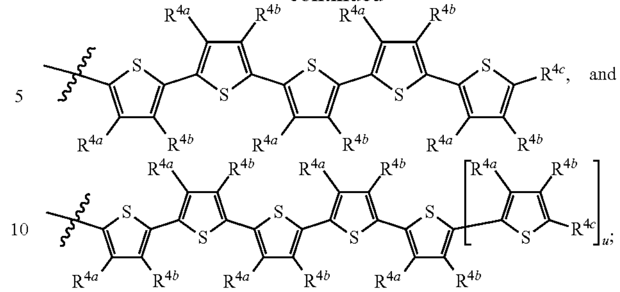

and u is an integer from 1 to 20;

$R^{2a}$, $R^{2b}R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

In certain embodiments of the first aspect of the invention, the metal-based coordination complex further comprises transferrin.

In certain embodiments of the first aspect of the invention, M is at least one of Ru, Rh, Os and Ir.

In certain embodiments of the first aspect of the invention, the metal-based coordination complex has the following structure:

TLD-1433

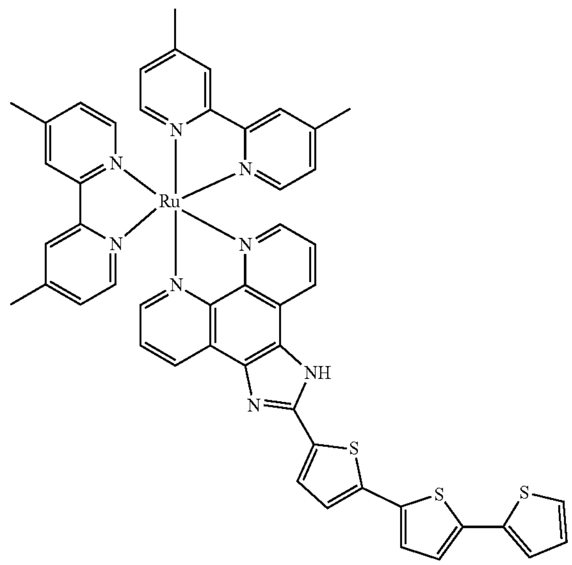

In certain embodiments of the first aspect of the invention, the metal-based coordination complex further comprises transferrin.

In certain embodiments of the first aspect of the invention, the immunogenic composition, wherein the immunogenic composition of the providing step is obtained from cell line cultures or from plasma from a donor infected with or previously infected with the immunogen.

In certain embodiments of the first aspect of the invention, the donor is a human other than the patient who is also a human.

In certain embodiments of the first aspect of the invention, the donor is the patient and is a human.

In certain embodiments, the first aspect of the invention further comprises exposing the metal-based coordination complex in the immunogenic composition to at least one of electromagnetic radiation and ultrasound effective to activate the metal-based coordination complex to inactivate or attenuate the immunogen.

In certain embodiments of the first aspect of the invention, the electromagnetic radiation is laser light having a wavelength from 500-950 nm.

In certain embodiments of the first aspect of the invention, the electromagnetic radiation is X-rays or Gamma rays.

In certain embodiments of the first aspect of the invention, the immunogen is at least one member selected from the group consisting of a microbe, a virus and components thereof In certain embodiments of the first aspect of the invention, the immunogen is an Influenza virus, a Zika virus or a coronavirus.

In certain embodiments of the first aspect of the invention, the immunogen is the SARS-CoV-2 virus.

In certain embodiments of the first aspect of the invention, the immunogenic composition is a monovalent, bivalent, multivalent or polyvalent vaccine effective to elicit a therapeutic and/or protective immune response against the immunogen.

A second aspect of the invention comprises a method for preparing an attenuated immunogenic composition, said method comprising: providing an immunogenic composition comprising an immunogen; and adding a metal-based coordination complex to the immunogenic composition to inactivate or attenuate the immunogen in the immunogenic composition to provide the attenuated immunogenic composition.

In certain embodiments of the second aspect of the invention, the metal-based coordination complex is represented by one of formulas (I), (VI), (VIIa) or (II) above.

In certain embodiments of the second aspect of the invention, the metal-based coordination complex further comprises transferrin.

In certain embodiments of the second aspect of the invention, the metal (M) of the metal-based coordination complex is at least one of Ru, Rh, Os and Ir.

In certain embodiments of the second aspect of the invention, the metal-based coordination complex has the following structure:

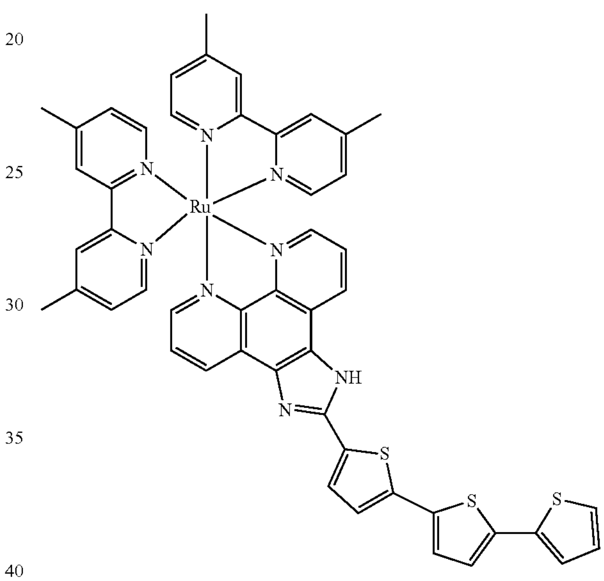

In certain embodiments, the second aspect of the invention further comprises exposing the metal-based coordination complex in the immunogenic composition to at least one of electromagnetic radiation and ultrasound effective to activate the metal-based coordination complex to inactivate or attenuate the immunogen.

In certain embodiments of the second aspect of the invention, the immunogen is at least one member selected from the group consisting of a microbe, a virus and components thereof In certain embodiments of the second aspect of the invention, the immunogen is an Influenza virus, a Zika virus or a coronavirus.

In certain embodiments of the second aspect of the invention, the immunogen is the SARS-CoV-2 virus.

In certain embodiments of the second aspect of the invention, the immunogenic composition is obtained from cell line cultures or from plasma from a donor infected with or previously infected with the immunogen.

In certain embodiments of the second aspect of the invention, the attenuated immunogenic composition is a monovalent, bivalent, multivalent or polyvalent vaccine effective to elicit a therapeutic and/or protective immune response against the immunogen.

A third aspect of the invention is an attenuated immunogenic composition prepared by the method of the invention.

In certain embodiments of the third aspect of the invention, the metal-based coordination complex further comprises transferrin and/or the immunogen is an Influenza virus, a Zika virus or a coronavirus.

In certain embodiments of the third aspect of the invention, the metal-based coordination complex further comprises transferrin and the immunogen is SARS-CoV-2.

In certain embodiments of the third aspect of the invention, the metal-based coordination complex has the following structure:

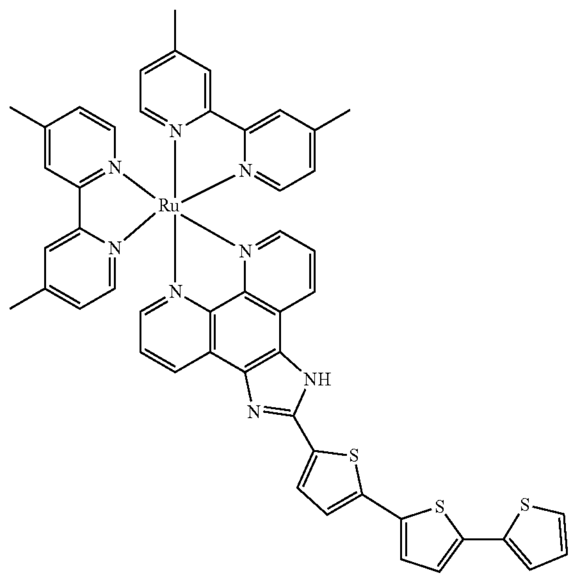

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (C) unless otherwise specified. All documents cited are in relevant part, incorporated herein by reference; the citation of any document is not to be construed as an admission that it is prior art with respect to the present invention.

BRIEF DESCRIPTION OF SEVERAL VIEWS OF THE DRAWINGS

The invention will be described in conjunction with the following drawings wherein:

FIG. 2 is a graph of percent survival of H1N1 against time of irradiation.

FIG. 3A is a graph of percent survival of H1N1 against PDC concentration without light activation.

FIG. 3B is a graph of percent survival of Zika Virus against PDC concentration without light activation.

FIG. 3C is a graph of percent survival of H1N1 against PDC concentration with light activation.

FIG. 3D is a graph of percent survival of Zika Virus against PDC concentration with light activation.

FIG. 4A is a graph of percent survival of Zika Virus against PDC concentration, wherein the concentration is on a logarithmic scale.

FIG. 4B is a graph of percent survival of Zika Virus against PDC concentration, wherein percent survival and concentration are on a logarithmic scale.

FIG. 5 is a graph of percent survival of Coronavirus against PDC concentration with and without light activation.

FIG. 6 is a graph of percent survival of Zika Virus against PDC concentration with and without light activation.

FIG. 7A is a graph of percent survival of Zika Virus against PDC concentration, wherein the concentration is on a logarithmic scale.

FIG. 7B is a graph of percent survival of Zika Virus against PDC concentration, wherein percent survival and concentration are on a logarithmic scale.

DETAILED DESCRIPTION OF PREFERRED EMBODIMENTS OF THE INVENTION

Glossary

Figure 1A:
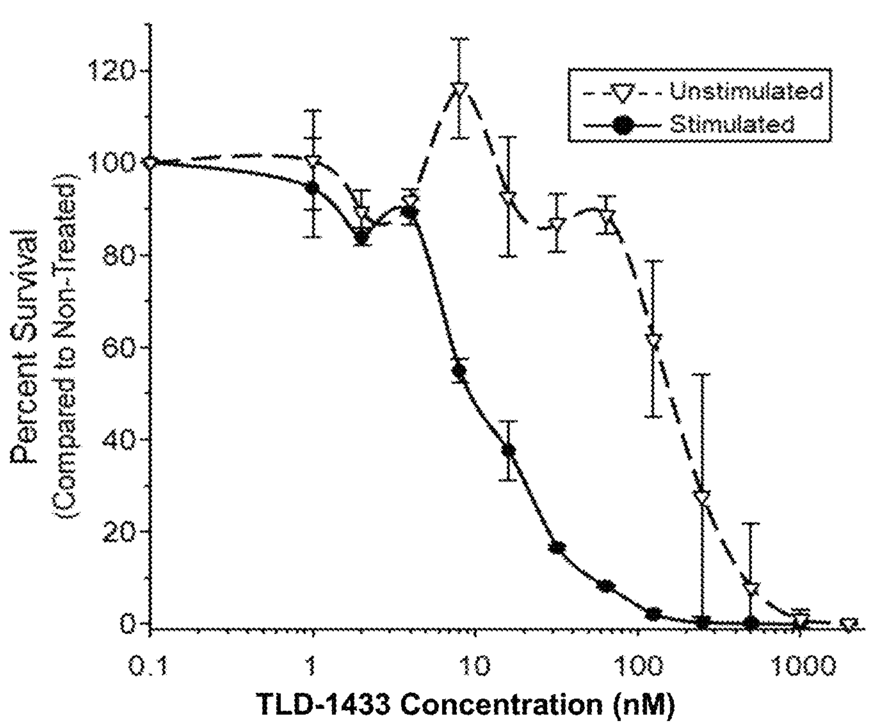
FIG. 1A is a graph of percent survival of Influenza A Virus H1N1 against PDC concentration, wherein the concentration is on a logarithmic scale.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously For the purposes of the present invention the terms "compound," "analog," and "composition of matter" stand equally well for the inventive compounds described herein, be they photodynamic or not, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms “treat” and “treating” and “treatment” as used herein, refer to partially or completely alleviating, inhibiting, ameliorating and/or relieving a condition from which a patient is suspected to suffer.

As used herein, “therapeutically effective” and “effective dose” refer to a substance or an amount that elicits a desirable biological activity or effect.

As used herein, the term “photodynamic therapy” refers to a treatment for destroying cells or modulating immune function, including immune response, of cells and tissue through use of a drug that can be activated by light of a certain wavelength and dose.

As used herein, the term “photodynamic compound” refers to a compound that provides photodynamic therapy.

As used herein, the term “immunotherapy” refers to a treatment which elicits an immune response from a patient so as to prevent, ameliorate or cure a condition (e.g., a disease or an infection).

Except when noted, the terms “subject” or “patient” are used interchangeably and refer to mammals such as human patients and non-human primates, as well as experimental animals such as rabbits, rats, and mice, and other animals. Accordingly, the term “subject” or “patient” as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

As used herein, the expression “biological target” refers to an organ, tissue and/or cell of an organism and/or to the organism itself As used herein the term “immunogenic” refers to a substance that is able to elicit an immune response.

Preparation Method

The invention provides a method for preparing a monovalent, bivalent, multivalent or polyvalent immunogenic composition (e.g., a vaccine), said method comprising: culturing microbes and/or virus(es) in cell lines with or without various media or collecting plasma from a donor infected with (or previously infected with) a particular microbial infection and/or virus to be treated, which comprises at least one of a microbe(s), virus(es), components of a microbe(s) and/or virus(es), adjuvant(s) and antibodies to the microbe(s) and/or virus(s), whether or not contained in plasma; and adding a metal-based coordination complex to the cultured microbe(s) and/or virus(es) or plasma to inactivate or attenuate any or all of the microbe(s) and/or cultured virus(es) with or without various media or plasma.

The cultured microbe(s) and/or virus(es) in cell lines with or without media or plasma collected from a donor infected with (or previously infected with) a particular microbe(s) and/or virus(es) to be treated. In certain embodiments, the pathogen is microbial. In other embodiments, the pathogen is a virus, preferably an enveloped virus and more preferably a coronavirus, including but not limited to SARS-CoV-2.

In the case of an autologous transplantation of plasma and/or components thereof including immunoglobulins, the donor is the patient. In this case, a patient diagnosed with a certain viral infection, such as COVID-19, will be injected with treated autologous plasma and/or plasma components to initiate a particular pathogen-specific adaptive immune response. This also would switch or reverse the patient’s immunosenescence towards active immunosurveillance. It is also within the scope of the invention to transplant plasma and/or plasma components from a donor who is not the patient, with a syngeneic transplant being most preferred when the transplantation is not autologous.

In the case of an allogeneic transplantation of plasma and/or plasma components, the donor is another patient. Treated allogeneic plasma harvested from patients with high protective antibodies titer will be transfused to a naïve (disease negative and/or asymptomatic) subject to create a passive protective immunity and/or the treated allogeneic plasma with a high titer of protective antibodies collected from a patient will be transfused to a naïve/asymptomatic subject to active an innate response and a long-lasting protective adaptive humoral immune response involving activation of T and B cells.

In another case of an allogeneic transplantation of plasma and/or plasma components, the donor is another patient. Treated allogeneic plasma and/or plasma components harvested from patients with high protective antibodies titer will be transfused to a patient with an active infection by inter-muscular injection to activate or modulate pathogen-specific adaptive immune responses.

In preferred embodiments, excitation of the metal-based coordination complex by, e.g., electromagnetic radiation, deactivates any virus in the plasma prior to implantation in the patient. Preferably, the metal-based coordination complex is a PDC that is photoactivated so as to generate reactive oxygen species. Photoactivation is preferably achieved by the application of light from a light source. Suitable light sources include but are not limited to lasers, light emitting diodes, fiber optics and lamps.

In certain embodiments, the metal-based coordination complex is activated by ionizing radiation in accordance with the teachings of U.S. Pat. No. 10,335,608 B2. The ionizing radiation is preferably at least one of X-rays and Gamma rays.

In certain embodiments, the metal-based coordination complex is activated by ultrasound in accordance with the teachings of the co-pending U.S. patent application of the same inventors, which is entitled "SONODYNAMIC THERAPY USING SONODYNAMICALLY ACTIVATED COORDINATION COMPLEXES OF TRANSITION METALS AS SENSITIZING AGENTS" and was filed on Mar. 4, 2021.

PDT dose parameters can be determined by a person of ordinary skill in the art with an understanding of the dosimetric and biological factors that govern therapeutic variability. See, e.g., Rizvi et al. "PDT Dose Parameters Impact Tumoricidal Durability and Cell Death Pathways in a 3D Ovarian Cancer Model." Photochemistry and photobiology. 2013; 89(4):942-952.

Factors to be considered include but are not limited to the amount of the PDC at the target site, tissue oxygenation, the molar extinction coefficient of the PDC at a chosen wavelength of light to produce a maximum level of singlet oxygen and/or ROS, target (e.g., tumor) localization, size, shape, vascular structure, etc. The following table lists PDT parameters to be adjusted and provides preferred, non-exhaustive, values for said parameters.

| PDT Parameter | Value |
|---|---|
| Wavelength (nm) | 200-1000 or 400-950 or 500-950 |
| Fluence ($J/cm^2$) | 0.01 to 100,000 or 1 to 10,000 or 10 to 1,000 |
| Irradiance ($mW/cm^2$) | 1 to 10,000 or 5 to 5,000 or 10 to 1,000 |
| Irradiation Time (secs) | 1 to 10,000 or 10 to 5,000 or 100 to 1,000 |

Activation of the metal-based coordination complex to deactivate immunogenic pathogens is preferably conducted extracorporeally.

The metal-based coordination complex is preferably at least one such compound disclosed in WO 2013158550 A1, WO 2014145428 A2, U.S. Pat. Nos. 6,962,910, 7,612,057, 8,445,475, 8,148,360 or US 20160206653 A1.

The metal of the metal-based coordination complex is at least one transition metal, which is preferably a Group 8 or 9 metal and is most preferably at least one of Ru, Rh, Os and Ir.

In certain embodiments, the metal-based coordination complex is combined with a metal-binding glycoprotein. Metal-binding glycoproteins suitable for use in the invention are capable of binding transition metals and delivering to a biological target said metals and other materials complexed with said metals. The metal-binding glycoproteins are preferably capable of binding Group 8 metals and/or Group 9 metals, and most preferably Ru, Os, Rh and Ir. Most preferred are the iron-binding glycoproteins transferrin, lactoferrin, ovotransferrin and melanotransferrin and variants thereof, with transferrin being most preferred. The glycoprotein can be purified from natural sources or can be from artificial sources. Thus, for example, the glycoprotein in certain embodiments is a recombinant transferrin, such as Apo-Transferrin or OPTIFERRIN, a recombinant human transferrin available from InVitria, a division of Ventria Bioscience. See US 20120088729 A1, Zhang et al., "Expression, purification, and characterization of recombinant human transferrin from rice (Oryza sativa L.)." Protein Expr Purif. 2010 November; 74(1):69-79. Epub 2010 May 4, and Steere et al., "Biochemical and structural characterization of recombinant human serum transferrin from rice (Oryza sativa L.)." J Inorg Biochem. 2012 Jul. 11; 116C:37-44. OPTIFERRIN is a particularly preferred glycoprotein as it increases the targeting and reduces the photobleaching of the metal-glycoprotein complexes of the invention.

In all of the embodiments provided herein, examples of suitable optional substituents are not intended to limit the scope of the claimed invention. The compounds of the invention may contain any of the substituents, or combinations of substituents, provided herein.

Method of Eliciting an Immune Response

The invention provides a method for eliciting an immune response in a patient, said method comprising the sequential steps of providing an immunogenic composition of at least one at least one of microbe(s), virus(es), components of a microbe(s) and/or virus(es), adjuvant(s) and antibodies to the microbe(s) and/or virus(s), whether or not contained in plasma; adding a metal-based coordination complex to the cultured microbe(s) and/or virus(es) or plasma to inactivate or attenuate any or all of the microbe(s) and/or cultured virus(es) with or without various media or plasma; and providing the immunogenic composition to a patient so as to elicit an immune response against the specific microbe(s) and/or virus(es).

The immunogen is preferably an enveloped virus, such as an Influenza virus, a Zika virus or a coronavirus, and the method preferably prevents or treats infections with such viruses.

The immunogenic composition is preferably administered in a pharmaceutically acceptable dosage form. The dosage form can further comprise at least one of diluents, extenders, carriers and the like. The dosage form is preferably a liquid, solid, gel or combination thereof. Suitable dosage forms; include, but are not limited to pills, tablets, capsules, eye drops and injectable liquids. The dosage form can be administered orally, rectally, topically, parenterally or intravenously. Administration can be systemic or localized (e.g., by injection into a tumor).

Some or all of the metal-based coordination complex can optionally be removed from the immunogenic composition prior to adminstration to the patient.

In certain embodiments, the immunogenic composition can further comprise at least one adjuvant to enhance the immune response. Suitable adjuvants include but are not limited to Transferrin binding proteins A and B, GMCSF expressing tumor cells lethally irradiated, Low dose cyclophosphamide (deplete Tregs), CpG oligodeoxyneucleotide (TLR9), Recombinant calreticulin, ATRA (all trans retinoic acid) (induces maturation of MDSC's), DBPMAF (serum vitamin D3-binding protein-derived macrophage activating factor), TNF-a, G-CSF (stimulate neutrophil), Γ-innulin (classical complement activator), Penicillin killed streptococci, Mycobacterium cell wall extract, BCG (live mycobacterial vaccine), Cryptosporidium parvam, Glycated Chitosan (polysaccharide preparation), Schizophyllan (Fungal β-glucan), Zymosan (yeast cell wall extract), Imiquimod (small molecule TLR-7 agonist), aluminum, alum and other adjuvants and immune check point blockers.

Immunogenic Composition

The invention provides an immunogenic composition. The composition can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the composition described herein.

The preparation methods described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry or by chromatography such as High Pressure Liquid Chromatography ("HPLC"), Gas Chromatography ("GC"), Gel-Permeation Chromatography ("GPC") or Thin Layer Chromatography ("TLC").

The invention will be illustrated in more detail with reference to the following Examples, but it should be understood that the present invention is not deemed to be limited thereto.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

Example 1

Inactivation of Influenza A Virus

Figure 1B:
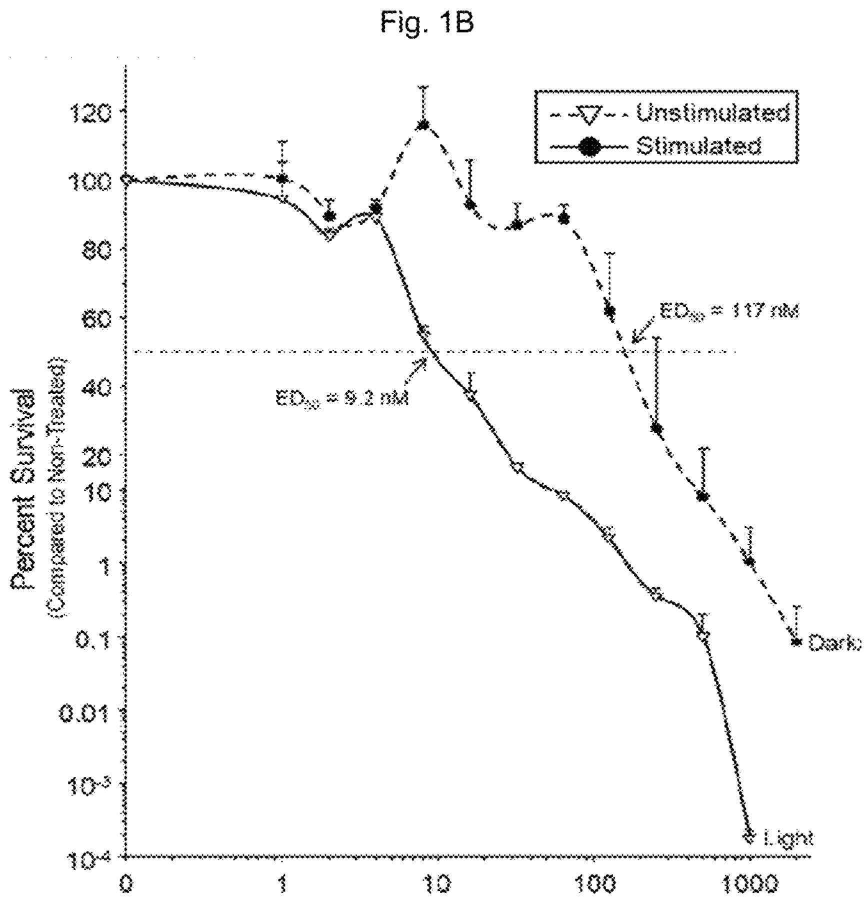
FIG. 1B is a graph of percent survival of Influenza A Virus H1N1 against PDC concentration, wherein percent survival and concentration are on a logarithmic scale.

Influenza A Virus ("IAV") H1N1 inactivation by different TLD-1433 concentrations was studied. Approximately $10^7$ Plaque-forming Unit ("PFU") of IAV was diluted >20-fold into a 1:1 mixture of Phosphate Buffered Saline ("PBS"): Dulbecco's Modified Eagle's Medium ("DMEM"). Lactoferrin was added to 32 ng/mL. TLD-1433 was added to the concentrations indicated in FIGS. 1A and 1B (X-axis). The mixtures were incubated 30 minutes, treated with green laser for 75 seconds, rested 20 minutes and then titrated for residual infectivity. The lines in FIGS. 1A and 1B represent average inactivation from a minimum of 3 replicates. The error bars represent the Standard Error of the Mean ("SEM"). The Y-axis is arithmetic in FIG. 1A and logarithmic in FIG. 1B to facilitate determinations of Inhibitory Concentration ("IC"), $IC_{80}$, $IC_{90}$, and $IC_{99}$ (used in the later kinetic experiments shown in FIG. 2).

These results clearly indicate that TLD-1433 has effects on planktonic solutions of H1N1 IAV in the nanomolar range and that the compound is more effective when light-activated. From these data, the concentrations required to inactivate various proportions of IAV are determined (see Table 1).

TABLE 1

TLD1433 concentrations required to achieve indicated Effective Doses (ED)

| | $ED_{50}$ | $ED_{80}$ | $ED_{90}$ | $ED_{95}$ | $ED_{99}$ | $ED_{99.5}$ |
|---|---|---|---|---|---|---|
| Average | 9.22 | 25.17 | 52.00 | 86.27 | 162.33 | 311.67 |
| SEM | 0.71 | 2.00 | 1.39 | 8.99 | 19.46 | 12.44 |

Many groups determine the Effective Dose ("ED") at inactivating 50% of the test subjects (ED50), but a more conservative ED80 is used by many other groups. As seen in Table 1, a TLD-1433 concentration of 25 nM can inactivate 80% of H1N1 virus and 162 nM inactivates 99% of IAV.

Example 2

Kinetics of H1 N1 Inactivation

Another useful parameter is to determine how quickly the PDC can inactivate the virus. For this purpose, we chose a constant TLD-1433 concentration of 220 nM (effective at inactivating >99% of virus under standard conditions of 32 ng/mL Lactoferrin and 75 seconds of laser activation) and varied the amount of laser exposure. Approximately 106 PFU of IAV was diluted >20-fold into a 1:1 mixture of PBS:DMEM. Lactoferrin was added to 32 ng/ml, TLD-1433 was added to 220 nM, and the mixtures were incubated 30 minutes. After incubation, the mixtures were treated with green laser for the periods of time indicated on the Y-axis of FIG. 2, rested 20 minutes and residual infectivity was determined. Lines represent average inactivation from 2 replicates. Error bars represent SEM. The results indicated a rapid killing of IAV, in which more than 50% of the virus is killed in the first few seconds. More than 90% of the virus was killed in less than 20 seconds.

Example 3

Inactivation of Influenza A Virus and Zika Virus

Approximately $10^7$ PFU of IAV or $10^5$ PFU of Zika Virus ("ZIKV") were diluted 50-fold into a 1:1 mixture of PBS: DMEM. Lactoferrin or Optiferrin was added to the concentrations indicated on the X-axes of FIGS. 3A, 3B, 3C and 3D. The mixtures were incubated 30 minutes. After incubation, the mixtures were treated with green laser for 75 seconds, rested 20 minutes and residual infectivity was determined. Lines represent average inactivation from 2 replicates. Error bars represent SEM.

Example 4

Inactivation of ZIKV as a Function of PDC Concentration

Approximately $10^5$ PFU of ZIKV were diluted >20-fold into a 1:1 mixture of PBS:DMEM. Lactoferrin was added to 32 ng/ml. TLD-1433 was added to the concentrations indicated on the X-axes of FIGS. 4A and 4B. The mixtures were incubated 30 minutes, treated with green laser for 75 seconds, rested 20 minutes and residual infectivity was determined. The Y-axis is arithmetic in FIG. 4A and logarithmic in FIG. 4B to facilitate determinations of $IC_{80}$, $IC_{90}$, and $IC_{99}$.

Example 5

Human coronavirus OC-43 stocks were treated with 32 μg/mL (L)-activator and with the concentrations of TLD-1433 shown in FIG. 5, then incubated 30 minutes, either activated or not as indicated, and residual virus infectivity was determined by immunofocus assay. Horizontal dashed line indicates 50% effective inhibitory dose; n=3; error bars are SEM.

Example 6

ZIKV was tested in accordance with the method of Example 4 with a fresher batch of TLD-1433. The results are shown in FIG. 6.

Example 7

Order of Addition Study

Tests were conducted to determine whether the order of addition of PDC and metal-binding glycoprotein would have an effect on ZIKV inactivation. The first experiment involved setting up a total of four sets. For two sets, 1 volume of ZIKV was added to 16 volumes of PBS. For two other sets, 1 volume of ZIKV was added to 16 volumes of Rabbit blood plasma.

One of each diluted virus set was then mixed with Lactoferrin to achieve a final concentration of approximately 32 μg/ml and dispensed into 96-well plates. A $1/50^{th}$ volume of appropriate 50×TLD-1433 was added into each well to achieve final TLD-1433 concentrations ranging from 0.1 to 316 nM. For the other diluted virus set, appropriate amounts of Lactoferrin and TLD-1433 were pre-mixed, virus was also dispensed into 96-well plates and the Lactoferin/TLD-1433 mixture then added to the virus. All sets were incubated for 30 minutes, treated with green laser for 75 seconds, rested for 20 minutes, and residual virus infectivity determined.

The results, which are shown in FIGS. 7A and 7B, suggest that the order of component mixing does not matter.

Example 8

Order of Addition Study

Figure 8:
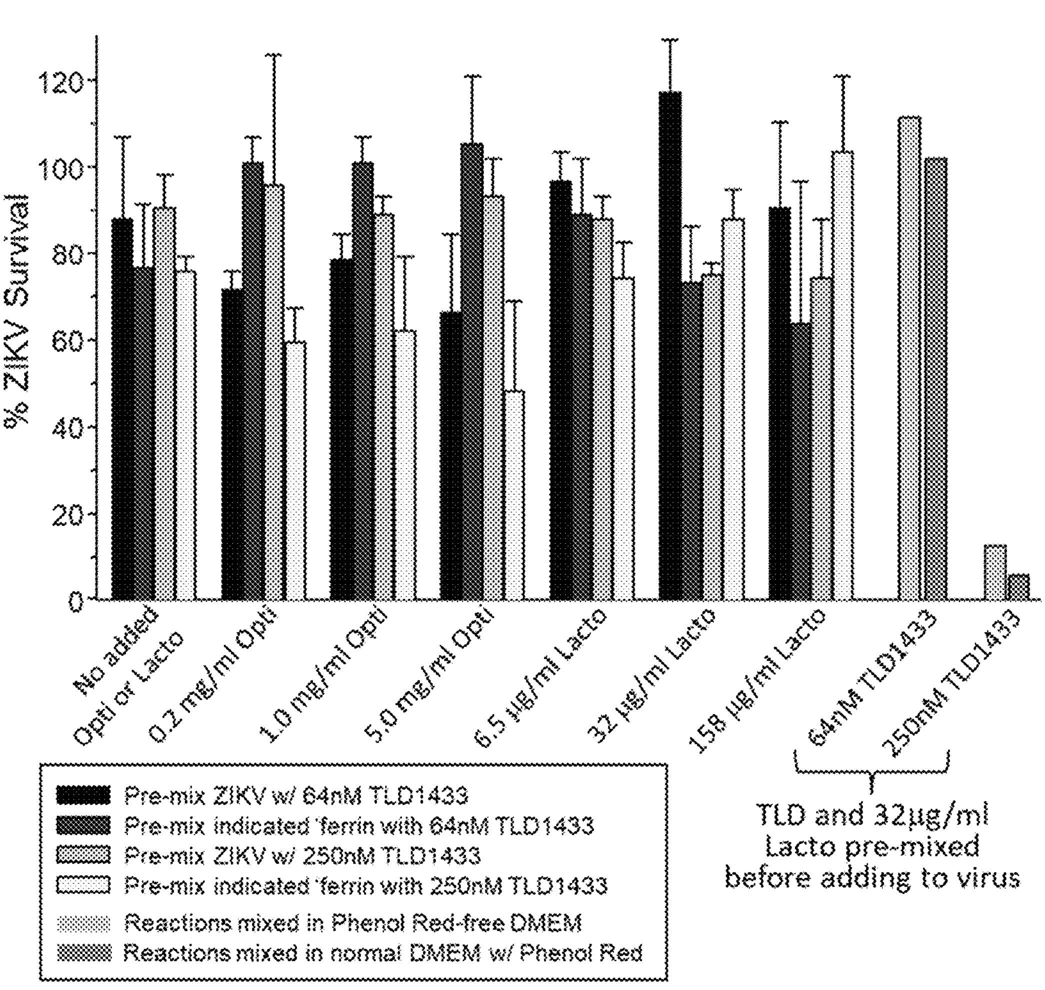
FIG. 8 is a bar chart showing the effect of order of addition or the presence of Phenol Red on Zika Virus inactivation.

To re-test whether component addition order matters, we set up another experiment, also attempting to optimize the amount of Optiferrin or Lactoferrin needed to inactivate virus in blood plasma. For this, there were eight sets, four treated with 64 nM TLD-1433 and various concentrations of either Optiferrin or Lactoferrin, and four treated with 250 nM TLD-1433 and various concentrations of Optiferrin/Lactoferrin (FIG. 8). Similar to above, two sets in each set of four had virus pre-mixed with the TLD-1433, this was dispensed into wells and the appropriate 'ferrin was added, whereas two other sets had the TLD-1433 and 'ferrin pre-mixed before adding to diluted virus already in wells.

Results also show, despite some variability, that the order of TLD/'ferrin addition generally does not seem to matter. Pre-mixing lower concentrations of Optiferrin with lower concentrations of TLD-1433 appeared to increase virus survival (red and black bars), and pre-mixing higher concentrations of Optiferrin with higher concentrations of TLD-1433 appeared to reduce virus survival (yellow bars) more, but the same cannot be said for higher concentrations of Lactoferrin combined with higher concentrations of TLD-1433. Furthermore, given the variability, none of these differences were significant by Student's T-test. The closest, with P-value 0.058, was comparison of the 64 nM TLD-1433 with 0.2 mg/ml Optiferrin, and, if anything, pre-mixing the components reduced virus killing capacity.

Example 9

Phenol Red Study

Testing was done to confirm whether the presence of phenol red in media had an effect upon TLD-1433 mediated ZIKV killing. For this experiment, ZIKV was diluted into either Phenol red-free DMEM, or into "normal" DMEM that contains phenol red. Sufficient Lactoferrin and TLD-1433 were pre-mixed to achieve 32 μg/ml Lactoferrin with either 64 or 250 nM TLD-1433 and then mixed with diluted virus, incubated, laser treated, rested and titrated. The results, shown in FIG. 8, suggest that the presence of phenol red enhances ZIKV killing.

Data from the various examples is summarized in Table 2 below.

TABLE 2

| | | Effective Dose to Inhibit Indicated % of Virus (nM ± SEM) | | | | |
|---|---|---|---|---|---|---|
| | | $ED_{50}$ | $ED_{80}$ | $ED_{90}$ | $ED_{99}$ | $ED_{99.9}$ |
| IAV | Dark | 157 ± 83 | 305 ± 166 | 460 ± 217 | 1920 ± 547 | nd |
| | Light | 9.2 ± 1.6 | 28 ± 3.1 | 53 ± 5.5 | 168 ± 48 | 497 ± 78 |
| ZIKV | Dark | 44 ± 7.1 | 153 ± 36 | 237 ± 53 | 628 ± 114 | nd |
| | Light | 12.0 ± 2.6 | 40 ± 9.0 | 61 ± 11.5 | 117 ± 27 | 322 ± 150 |
| CoV | Dark | 78 ± 7.5 | 107 ± 5 | 128 ± 8 | 232 ± 46 | 389 ± 107 |
| | Light | 3.3 ± 0.9 | 4.9 ± 0.7 | 6.7 ± 1.0 | 23 ± 1.2 | 61 ± 4.6 |

CoV (Biological Safety Level ("BSL")-2) appears to be much more sensitive to the action of the light-activated PDC, with a dose of 3.3 nM needed to inactivate 50%, whereas 9.2 nM is needed to inactivate the same amount of IAV and 12 nM is needed to inactivate ZIKV. Similarly, the amounts of PDC required to inactivate 99.9% of each virus are 61 nM for CoV, 322 nM for ZIKV and 497 nM for IAV. Thus, the PDC is 3 to 5 times more potent against CoV (BSL-2) compared to the other tested viruses. The compound also is effective without light activation, but on average, light activation results in a 4.2-fold enhancement of ZIKV inactivation, a 12-fold enhancement of IAV inactivation and an 18.7-fold enhancement of CoV inactivation.

Example 10

Prophylactics (Vaccine)—Prophetic a) Allogeneic plasma harvested from COVID-19 patients with high protective antibodies titer will be treated by PDT (i.e., with TLD-1433/transferrin and laser activation) and transfused to naïve/asymptomatic subjects (i.e., disease negative and/or asymptomatic or "healthy" subjects) to create a passive protective immunity, and/or simultaneously b) the PDT treated allogeneic plasma with high titer of protective antibodies collected from COVID-19 patients will be transfused to naïve/asymptomatic subjects to activate an innate response and a long lasting protective adaptive humoral immune responses involving activation of T and B cells.

Example 11

PDT Treated Plasma-Derived Therapy—Prophetic

The same allogeneic strategy as described in Example 1 will be applied for an active treatment of infection, because the PDT treated plasma is from both a) an attenuated live and/or inactivated virus and b) a high titer of virus specific antibodies; hence, the PDT treated plasma collected from a patient with COVID-19 will be injected Inter-Muscular ("IM") to activate (boost) or modulate pathogen-specific adaptive immune responses and to switch or reverse immunoquiescence and/or immunosenescence toward active immunosurveillance in the patient.

Example 12

Autologous Plasma Approach—Prophetic

Autologous plasma from patients will be used to boost and/or reprogram their immune systems via PDT treated plasma cells and COVID-19 virus-induced Damage-Associated Molecular Patterns ("DAMPs"). In this example, patients diagnosed with COVID-19 will be injected IM with their own plasma after PDT treatment to initiate a particular pathogen-specific adaptive immune responses and to switch or reverse their immunoquiescence and/or immunosenescence toward active immunosurveillance. Restoration of immune system could be extremely beneficial in maximizing protective immune responses to COVID-19 in older adults and/or immunocompromised patients.

Methodology—Prophetic

Preparation of Vaccine from Allogeneic Plasma

Plasma is tested to detect high levels of COVID-19 specific antibodies using am Enzyme Linked Immuno Sorbent Assay ("ELISA") test.

Plasma is harvested when the SARS-CoV-2 neutralizing antibodies titer gets above 1:640.

The harvested plasma (approximately 240 ml) is treated with TLD-1433/transferrin in combination with 530 nm (green) laser light at doses effective to attenuate or neutralize the coronavirus.

After the PDT treatment, the allogeneic plasma will be tested for safety and levels of neutralizing (protective) antibodies.

Characterized plasma will be: (a) Transfused (IntraVenous ("IV")), following the Good Manufacturing Practices ("GMP") requirements, as per FDA guidance or injected IM, up to 10 cc of the plasma. When injected into a new patient or administered to an asymptomatic subject, the PDT plasma-derived therapy will provide "passive immunity" until the patient's immune system can generate its own antibodies (adaptive immunity) induced by the PDT treated plasma injected IM.

The following methodology will be followed to convert autologous plasma into an effective therapeutic.

10 cc of the autologous plasma is collected from a patient who has been previously diagnosed with COVID-19. The plasma is treated with TLD-1433/Rutherrin® in combination with 530 nm (green) laser light at doses to attenuate or neutralize the coronavirus After the treatment, the autologous plasma will be tested for safety and levels of neutralizing (protective) antibodies.

The characterized plasma will be injected IM, up to 10 cc of the plasma.

The invention will not require researchers to discover which antibodies are most effective at destroying the novel coronavirus, as the entire disease-fighting army of protective and pathogen specific antibodies is imported from patients whose bodies have already successfully fought the disease.

Viruses, including SARS-CoV-2 are continuously changing and mutating as a result of genetic selection. They undergo subtle genetic changes through mutation and major genetic changes when an error is incorporated in the viral genome. Mutations can produce viruses with new antigenic determinants. The appearance of an antigenically novel virus through mutation is called antigenic drift. Antigenically altered viruses may be able to cause disease in previously resistant or immune hosts. The invention will automatically adjust for antigenic drift, by using the body's entire disease-fighting army of protective and pathogen specific antibodies to combat the disease.

While the invention has been described in detail and with reference to specific examples thereof, it will be apparent to one skilled in the art that various changes and modifications can be made therein without departing from the spirit and scope thereof.

What is claimed is:

1. A method for eliciting an immune response in a patient, said method comprising the sequential steps of:

adding a metal-based coordination complex to an immunogenic composition comprising an immunogen to prepare an inactivated immunogenic composition in which the immunogen is inactivated; and administering the inactivated immunogenic composition to the patient so as to elicit the immune response against the immunogen, wherein the immunogen is a virus or an immunogenic viral component, and the metal-based coordination complex has the following structure:

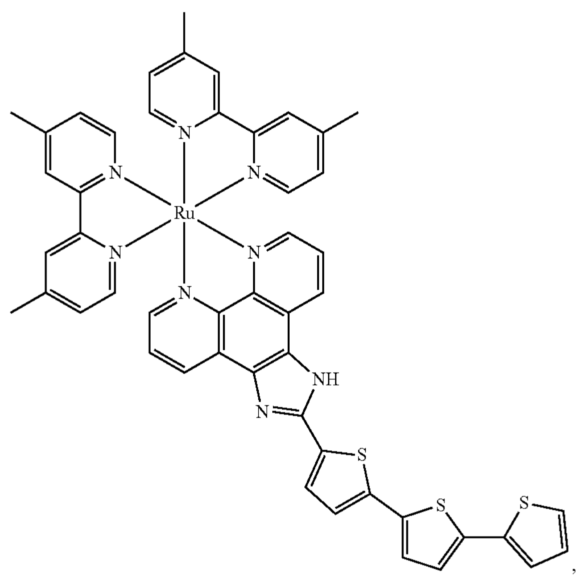

including hydrates, solvates, pharmaceutically acceptable salts, prodrugs and complexes thereof.

2. The method of claim 1, wherein the metal-based coordination complex further comprises transferrin.

3. The method of claim 1, wherein the immunogenic composition is obtained from cell line cultures or from plasma from a donor infected with or previously infected with the immunogen.

4. The method of claim 3, wherein the donor is a human other than the patient who is also a human.

5. The method of claim 3, wherein the donor is the patient and is a human.

6. The method of claim 1, further comprising exposing the metal-based coordination complex in the immunogenic composition to at least one of electromagnetic radiation and ultrasound effective to activate the metal-based coordination complex to inactivate the immunogen.

7. The method of claim 6, wherein the electromagnetic radiation is laser light having a wavelength from 500-950 nm.

8. The method of claim 6, wherein the electromagnetic radiation is X-rays or Gamma rays.

9. The method of claim 1, wherein the immunogen is an Influenza virus, a Zika virus or a coronavirus.

10. The method of claim 9, wherein the immunogen is the SARS-COV-2 virus.

11. The method of claim 1, wherein the inactivated immunogenic composition is a monovalent, bivalent, multivalent or polyvalent vaccine effective to elicit a therapeutic and/or protective immune response against the immunogen.

12. The method of claim 1, wherein the metal-based coordination complex further comprises chloride ions.

13. A method for preparing an inactivated immunogenic composition, said method comprising:

providing an immunogenic composition comprising an immunogen, which is a virus or an immunogenic viral component; and adding a metal-based coordination complex to the immunogenic composition to inactivate the immunogen in the immunogenic composition to provide the inactivated immunogenic composition, wherein the metal-based coordination complex has the following structure:

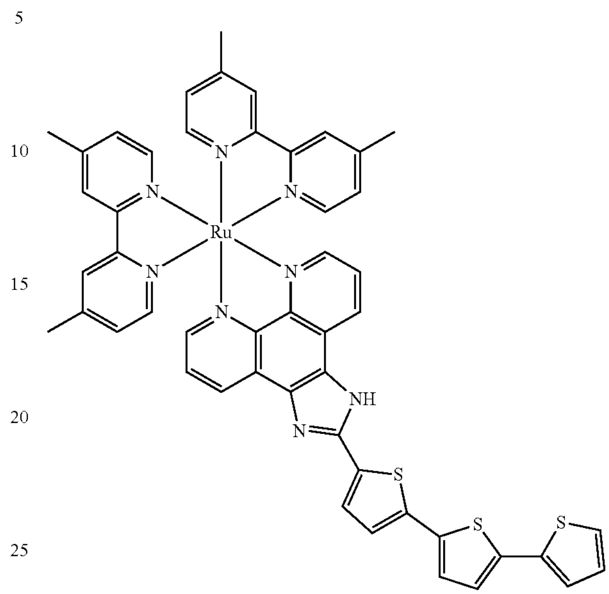

including hydrates, solvates, pharmaceutically acceptable salts, prodrugs and complexes thereof.

14. The method of claim 13, wherein the metal-based coordination complex further comprises transferrin.

15. The method of claim 13, further comprising exposing the metal-based coordination complex in the immunogenic composition to at least one of electromagnetic radiation and ultrasound effective to activate the metal-based coordination complex to inactivate the immunogen.

16. The method of claim 13, wherein the immunogen is an Influenza virus, a Zika virus or a coronavirus.

17. The method of claim 13, wherein the immunogen is the SARS-COV-2 virus.

18. The method of claim 13, wherein the immunogenic composition is obtained from cell line cultures or from plasma from a donor infected with or previously infected with the immunogen.

19. The method of claim 13, wherein the inactivated immunogenic composition is a monovalent, bivalent, multivalent or polyvalent vaccine effective to elicit a therapeutic and/or protective immune response against the immunogen.

20. An inactivated immunogenic composition prepared by the method of claim 13.

21. The inactivated immunogenic composition of claim 20, wherein the metal-based coordination complex further comprises transferrin and the immunogen is an Influenza virus, a Zika virus or a coronavirus.

22. The inactivated immunogenic composition of claim 20, wherein the metal-based coordination complex further comprises transferrin and the immunogen is SARSCoV-2.

23. The inactivated immunogenic composition of claim 20, wherein the metal-based coordination complex further comprises chloride ions.

24. The method of claim 13, wherein the metal-based coordination complex further comprises chloride ions.

* * * * *